United States Patent [19]

Brunavs et al.

[11] Patent Number: 5,480,873
[45] Date of Patent: Jan. 2, 1996

[54] PHARMACEUTICAL COMPOUNDS

[75] Inventors: Michael Brunavs, Frimley; Colin P. Dell, Dorking; David R. Dobson; Peter T. Gallagher, both of Camberley; Terence A. Hicks, Fleet; William M. Owton, Lightwater; Colin W. Smith, Bracknell, all of England

[73] Assignee: Lilly Industries Limited, Basingstoke, England

[21] Appl. No.: 23,220

[22] Filed: Feb. 25, 1993

[30] Foreign Application Priority Data

Feb. 28, 1992 [GB] United Kingdom .................... 9204302
Oct. 28, 1992 [GB] United Kingdom .................... 9222650

[51] Int. Cl.$^6$ .......................... C07C 50/18; C07C 50/20; A61K 31/12
[52] U.S. Cl. .......................... 514/33; 514/381; 514/382; 536/17.3; 536/17.4; 546/112; 546/285; 548/250; 548/252; 548/253; 548/254; 548/145; 548/214; 548/204; 548/300.4; 548/235; 548/236; 552/209; 552/221; 552/224; 552/227; 552/234; 552/235; 552/236; 552/237; 552/248; 552/241; 552/243; 552/244; 552/245; 552/246; 552/261; 552/262
[58] Field of Search ..................... 552/209, 221, 552/224, 227, 234, 235, 236, 237, 248, 241, 243, 244, 245, 246, 261, 262; 546/112, 285; 548/250, 252, 253, 254, 145, 214, 204, 300.4, 235, 236, 247; 536/17.3, 17.4; 514/381, 382, 33

[56] References Cited

U.S. PATENT DOCUMENTS

| | | | |
|---|---|---|---|
| 3,752,813 | 8/1973 | Shen et al. ................................ | 260/267 |
| 3,984,429 | 10/1976 | Peel et al. ............................ | 260/308 D |
| 3,984,534 | 10/1976 | Peel et al. .................................... | 424/45 |
| 4,226,784 | 10/1980 | Kalopissis et al. ...................... | 260/378 |
| 4,244,968 | 1/1981 | Friedmann ................................ | 424/308 |
| 4,950,687 | 8/1990 | Dall 'Asta et al. ...................... | 514/548 |

FOREIGN PATENT DOCUMENTS

| | | |
|---|---|---|
| 0243968 | 11/1987 | European Pat. Off. . |
| 0253144 | 1/1988 | European Pat. Off. . |
| 2711493 | 10/1977 | Germany . |
| WO92/10464 | 6/1992 | WIPO .......................... C07C 69/96 |
| WO92/16496 | 10/1992 | WIPO .......................... C07C 235/66 |

OTHER PUBLICATIONS

*Chemical Abstracts*, vol. 31, Abstract No. 3040(7), 1937.
Mosby, et al., "Products of Nucleophilic Displacement Reactions in the Anthraquinone Series", *Tetrahedron*, vol. 8, pp. 107–115, 1960.
Slavík, et al., "Substitution of NH Hydrogen in Nitrogen Derivatives of Polycyclic Hydrocarbons and Quinones", *Coll. Czech. Chem. Comm.*, vol. 4, No. 40, pp. 1193–1198, 1975.
*Chemical Abstracts*, vol. 84, No. 6 Abstract No. 32527c, p. 78, 1976.
Budziarek, Richard, "The Reaction of Sodium Sulphite and Bisulphite with Nitro- and Hydroxylamino- Anthraquinones", *Chem. Ind.*, No. 15, pp. 583–584, 1978.
Alexander, et al., "Methylation and Hydroxylation Studies on Aloe-emodin", *J. Org. Chem.*, No. 45, pp. 20–24, 1980.
*Chemical Abstracts*, vol. 92, No. 1, Abstract No. 6302W, pp. 592–593, 1980.
*Chemical Abstracts*, vol. 95, No. 17, Abstract No. 150250g, p. 628, 1981.
Summers, et al., "Hydroxamic Acid Inhibitors of 5-Lipoxygenase: Quantitative Structure–Activity Relationships", *J. Med. Chem.* vol. 33, No. 3, pp. 992–998, 1990.
*Beilsteins Handbuch der Organischen Chemie*, 4th Edition, 3rd Supplement, vol. 10, Part 5, pp. 4787–4790, 1972.
Arai et al., "Amide Ion Formation and N-Alkylation of Aminoanthraquinones in the Presence of Potassium Hydroxide in Dimethyl Sulfoxide", *Bull. Chem. Soc. Japan*, 58(5), 1458–1463 (1985).
Dreyfus, et al., "Synthèse de substances macromoléculaires renfermant des motifs monomères dérivés de colorants", *Bull. Soc. Chem. France*, 5–6, 1196–1200 (1975).
Katzhendler, et al., "Synthesis of aminoanthraquinone derivatives and their in vitro evaluation as potential anti-cancer drugs", *Eur. J. Med. Chem.*, 24, 23–30 (1989).
Peters, et al., "Structure–property relationships in 1,2,4-tri-donor-substituted anthraquinones–2-amino-1,4-dihydroxyanthraquinones", *J. Soc. Dyers Colour*, 105, 315–321 (1989).

(List continued on next page.)

*Primary Examiner*—Kimberly J. Kestler
*Attorney, Agent, or Firm*—James P. Leeds

[57] ABSTRACT

Pharmaceutical compounds of the formula

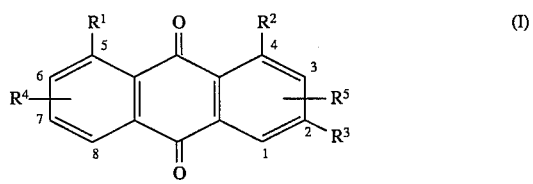

in which

R$^1$ and R$^2$ are each hydrogen, hydroxyl, halo, C$_{1-4}$ alkyl, C$_{1-4}$ alkoxy, acyloxy, —O-glucoside, optionally substituted phenyl or optionally substituted phenyl-C$_{1-4}$ alkoxy;

R$^3$ is tetrazolyl, or and R$^4$ and R$^5$ are each hydrogen, hydroxy, acyloxy, nitro, C$_{1-4}$ alkyl, C$_{1-4}$ alkoxy, halo, optionally substituted phenyl, —SO$_3$H or —NR'R" where R' and R" are each hydrogen or C$_{1-4}$ alkyl;

provided that when R$^3$ is —CR'R".CHR'''CO$_2$H or tetrazolyl, R$^1$ and R$^2$ are each hydroxyl, halo, C$_{1-4}$ alkyl, C$_{1-4}$ alkoxy, acyloxy, —O-glucoside, optionally substituted phenyl or optionally substituted phenyl C$_{1-4}$ alkoxy; and or a pharmaceutically acceptable salt or ester thereof.

9 Claims, No Drawings

OTHER PUBLICATIONS

Castle, et al., "The Synthesis of some Monomethylanthracenamines", *Chem. Abstr,* 116:105789f (1992).

Sal'nikova, et al., "Substituted Amedic of 2–anthraquinonesuccinamenic acid: Synthesis and Study of Their Pharmacological Activity", *Chem. Abstr.,* 113:204406 (1990).

Alemayehu, et al., "Quinones of Senna didymobotrya", *Chem. Abstr.,* 112:52218c (1990).

Horner, et al., "Corrosion Inhibitors 23(1)", *Chem. Abstr.,* 90:91154a (1979).

Metwally, "Reaction of Hydroxymethylanthraquinones with Thionyl Chloride", *J. Appl. Chem. Biotechnol.,* 25, 161–168 (1975).

Alexander, et al., "Methylation and Hydroxylation Studies on Aloe–emodin", *J. Org. Chem.,* 45, 20–24 (1980).

Yamada, et al., "Electrophotographic Photoreceptor Using Disazo Compound Charge–generating Agent", *Chem. Abstr.* 115:194178a(1991) of JP03 69,962.

Hayashi, et al., "Colored Rubbers and Rubber Additives", *Chem. Abstr., 113:25368r (1990).*

Proter, Derwent Abstract 84–020099/04 or J5 8210–009–A (1984).

Proter, Derwent Abstract 83–17972k/08 of FR 2508–798 (1983).

Proter, Derwent Abstract 79–66382B/37 of BE–875–945 (1979).

Antonello, et al., "Diethylaminopropionamide–hydroxy–anthraquinones as Potential Anticancer Agents: Synthesis and Characterization", *Arch. Pharm.* (Weinheim), 322, 541–544 (1989).

PHARMACEUTICAL COMPOUNDS

This invention relates to pharmaceutical compounds and their preparation.

There are many anthraquinone (9,10-dihydro-9,10-dioxoanthracene) compounds disclosed in the literature and they are described as having a variety of uses. British Patent 1 578 452 discloses some compounds of this type which are related to the well-known compound rhein.

The present invention relates to pharmaceutical compounds of the formula (I)

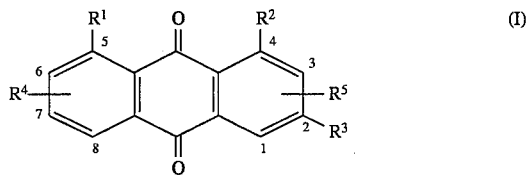

in which $R^1$ and $R^2$ are each hydrogen, hydroxyl, halo, $C_{1-4}$ alkyl, $C_{1-4}$ alkoxy, acyloxy, —O-glucoside, optionally substituted phenyl or optionally substituted phenyl-$C_{1-4}$ alkoxy;

$R^3$ is
—$CO_2H$,
—NR'$SO_2$R" where R' is hydrogen or $C_{1-4}$ alkyl and R" is hydroxyl, $C_{1-4}$ alkyl or optionally substituted phenyl,
—CONR'R" where R' and R" are each hydrogen, $C_{1-4}$ alkyl, acyl or optionally substituted phenyl,
—CONR'OR" where R' is $C_{1-4}$ alkyl or optionally substituted phenyl and R" is $C_{1-4}$ alkyl or benzyl,
—CR'R".CR'....(NHR"")$CO_2H$ where R" and R" are each hydrogen, $C_{1-4}$ alkyl or optionally substituted phenyl, R'" is hydrogen, —$CO_2H$ or —$C_{1-4}$ alkylene—$CO_2H$, and R"" is hydrogen or acyl,
—CR'R".CHR'" $CO_2H$ where R' and R" are each hydrogen or $C_{1-4}$ alkyl and R'" is optionally substituted phenyl,
—CR'R"S(O)$_n$R'" where R' and R" are each hydrogen or $C_{1-4}$ alkyl, R'" is optionally substituted phenyl and n is 0, 1 or 2,
—$PO_3$R'R" where R' and R" are each hydrogen, $C_{1-4}$ alkyl or optionally substituted phenyl,
—CR'R"—$PO_3$R'"R"" where R', R", R'" and R"" are each hydrogen, $C_{1-4}$ alkyl or optionally substituted phenyl,
—CH=CH—$PO_3$R'R" where R' and R" are each hydrogen, $C_{1-4}$ alkyl or optionally substituted phenyl,

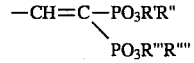

where R', R", R'" and R"" are each hydrogen, $C_{1-4}$ alkyl or optionally substituted phenyl,

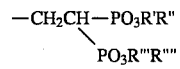

where R', R", R'" and R"" are each hydrogen, $C_{1-4}$ alkyl or optionally substituted phenyl,
—CH=CHR' where R' is —$CO_2H$, nitrile, tetrazolyl, optionally substituted benzimidazol-2-yl, optionally substituted N-$C_{1-4}$ alkyl benzimidazol-2-yl, optionally substituted oxazol-5-yl, optionally substituted thiazol-5-yl, optionally substituted isoxazol-5-yl, optionally substituted isothiazol-5-yl or optionally substituted oxadiazol-2-yl,
tetrazolyl, or
pyridyl, optionally substituted benzimidazol-2-yl, optionally substituted N-$C_{1-4}$ alkyl benzimidazol-2-yl, optionally substituted oxazol-5-yl, optionally substituted thiazol-5-yl, optionally substituted isoxazol-5-yl, optionally substituted isothiazol-5-yl or optionally substituted oxadiazol-2-yl; and $R^4$ and $R^5$ are each hydrogen, hydroxy, acyloxy, nitro, $C_{1-4}$ alkyl, $C_{1-4}$ alkoxy, halo, optionally substituted phenyl, —$SO_3H$ or —NR'R" where R' and R" are each hydrogen or $C_{1-4}$ alkyl;

provided that when $R^3$ is —CR'R".CHR'"$CO_2H$ or tetrazolyl, $R^1$ and $R^2$ are each hydroxyl, halo, $C_{1-4}$ alkyl, $C_{1-4}$ alkoxy, acyloxy, —O-glucoside, optionally substituted phenyl or optionally substituted phenyl $C_{1-4}$ alkoxy; and provided that when $R^3$ is $CO_2H$, the 9,10-dihydro-9,10-dioxoanthracene nucleus is substituted by (1) 1,4,5-trihydroxy, (2) 1,4,5-triacetoxy, (3) 1,4,5,8-tetramethoxy, (4) 1,4,5,8-tetrahydroxy, (5) 1,4,5,8-tetracetoxy, (6) 1,4-dimethoxy, (7) 1-acetoxy-4-hydroxy, (8) 4,5-dihydroxy-8-fluoro, (9) 4,5-dimethoxy-8-fluoro, (10) 4,5-dimethoxy-6-fluoro, (11) 4,5-dihydroxy-6 -fluoro, (12) 3,6-difluoro-4,5-dimethoxy, (13) 1,4,5-trimethoxy, (14) 1,4-dihydroxy, (15) 1,4-diacetoxy and (16) 4,5-dimethoxy;

and salts and esters thereof.

Such compounds are useful as pharmaceuticals. They modify cell function, and are indicated for use in the treatment of skeletal diseases, diabetes and complications. In particular, the compounds are indicated for treating rheumatoid arthritis, and connective tissue matrix diseases such as osteoarthritis.

With the exception of a small number of compounds, the above compounds of formula (I) are novel. Furthermore, the invention also provides certain compounds which are intermediates in the preparation of pharmaceutical compounds of formula (I), in which $R^3$ is —$NH_2$, —CHO, —CN, and —CH=NOR' where R' is hydrogen, $C_{1-4}$ alkyl or acyl. Thus the invention also provides compounds of the formula (I) above, in which $R^1$ and $R^2$ are each hydrogen, hydroxy, halo, $C_{1-4}$ alkyl, $C_{1-4}$ alkoxy, acyloxy, —O-glucoside, optionally substituted phenyl or optionally substituted phenyl-$C_{1-4}$ alkyloxy;

$R^3$ is
—$CO_2H$,
—NR'$SO_2$R" where R' is hydrogen or $C_{1-4}$ alkyl and R" is hydroxyl, $C_{1-4}$ alkyl or optionally substituted phenyl, —CONR'R" where R' and R" are each hydrogen, $C_{1-4}$ alkyl, acyl or optionally substituted phenyl,
—CONR'OR" where R' is $C_{1-4}$ alkyl or optionally substituted phenyl and R" is $C_{1-4}$ alkyl or benzyl,
—CR'R".CR'" (NHR"")$CO_2H$ where R' and R" are each hydrogen, $C_{1-4}$ alkyl or optionally substituted phenyl, R'" is hydrogen, —$CO_2H$ or —$C_{1-4}$ alkylene—$CO_2H$, and R"" is hydrogen or acyl,
—CR'R".CHR'"$CO_2H$ where R' and R" are each hydrogen or $C_{1-4}$ alkyl and R'" is optionally substituted phenyl,
—CR'R"S(O)$_n$R'" where R' and R" are each hydrogen or $C_{1-4}$ alkyl, R'" is optionally substituted phenyl and n is 0, 1 or 2, —$PO_3R'R''$ where R' and R'' are each hydrogen, $C_{1-4}$ alkyl or optionally substituted phenyl, —$CR'R''$—$PO_3R'''R''''$ where R', R'', R''' and R'''' are each hydrogen, $C_{1-4}$ alkyl or optionally substituted phenyl, —$CH$=$CH$—$PO_3R'R''$ where R' and R'' are each hydrogen, $C_{1-4}$ alkyl or optionally substituted phenyl,

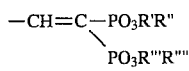

where R', R'', R''' and R'''' are each hydrogen, $C_{1-4}$ alkyl or optionally substituted phenyl,

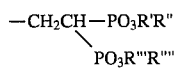

where R', R'', R''' and R'''' are each hydrogen, $C_{1-4}$ alkyl or optionally substituted phenyl, —$CH$=$CHR'$ where R' is —$CO_2H$, nitrile, tetrazolyl, optionally substituted benzimidazol-2-yl, optionally substituted N-$C_{1-4}$ alkyl benzimidazol-2-yl, optionally substituted oxazol-5-yl, optionally substituted thiazol-5-yl, optionally substituted isoxazol-5-yl, optionally substituted isothiazol-5-yl or optionally substituted oxadiazol-2-yl, tetrazolyl, pyridyl, optionally substitued benzimidazol-2-yl, optionally substituted N-$C_{1-4}$ alkyl benzimidazol-2-yl, optionally substituted oxazol-5-yl, optionally substituted thiazol-5-yl, optionally substituted isoxazol-5-yl, optionally substituted isothiazol-5-yl or optionally substituted oxadiazol-2-yl,

—$NH_2$,

—CHO,

—CN, or

—$CH$=$NOR'$ where R' is hydrogen, $C_{1-4}$ alkyl or acyl; and $R^4$ and $R^5$ are each hydrogen, hydroxy, acyloxy, nitro, $C_{1-4}$ alkyl, $C_{1-4}$ alkoxy, halo, optionally substituted phenyl, —$SO_3H$, or —NR'R'' where R' and R'' are each hydrogen or $C_{1-4}$ alkyl;

provided that when $R^3$ is —$CR'R''.CHR'''CO_2H$, —CN or tetrazolyl, $R^1$ and $R^2$ are each hydroxyl, halo, $C_{1-4}$ alkyl, $C_{1-4}$ alkoxy, acyloxy, —O-glucoside, optionally substituted phenyl or optionally substituted phenyl-$C_{1-4}$ alkoxy;

provided that when $R^3$ is $CO_2H$, the 9,10-dihydro-9,10-dioxoanthracene nucleus is substituted by (1) 1,4,5-trihydroxy, (2) 1,4,5-triacetoxy, (3) 1,4,5,8-tetramethoxy, (4) 1,4,5,8-tetrahydroxy, (5) 1,4,5,8-tetraacetoxy, (6) 1,4-dimethoxy, (7) 1-acetoxy-4-hydroxy, (8) 4,5-dihydroxy-8-fluoro, (9) 4,5-dimethoxy-8-fluoro, (10) 4,5-dimethoxy-6-fluoro, (11) 4,5-dihydroxy-6-fluoro, and (12) 3,6-difluoro-4,5-dimethoxy;

provided that when $R^3$ is —$NH_2$, $R^1$ and $R^2$ are hydroxy or $R^1$ and $R^2$ are methoxy and $R^4$ and $R^5$ are hydrogen; and provided that when $R^3$ is —CHO, $R^1$ and $R^2$ are methoxy and $R^4$ and $R^5$ are hydrogen;

and salts and esters thereof.

A particular group of compounds according to the invention is of formula (I) above, in which $R^1$ and $R^2$ are each hydrogen, hydroxyl, halo, $C_{1-4}$ alkyl, $C_{1-4}$ alkoxy, acyloxy, —O-glucoside or optionally substituted phenyl;

$R^3$ is

—$NR'SO_2R''$ where R' is hydrogen or $C_{1-4}$ alkyl and R'' is hydroxyl, $C_{1-4}$ alkyl or optionally substituted phenyl, —$CONR'R''$ where R' and R'' are each hydrogen, $C_{1-4}$ alkyl or optionally substituted phenyl, —$CONR'OR''$ where R' is $C_{1-4}$ alkyl or optionally substituted phenyl and R'' is $C_{1-4}$ alkyl or benzyl, —$CR'R''.CH(NH_2)CO_2H$ where R' and R'' are each hydrogen, $C_{1-4}$ alkyl or optionally substituted phenyl, —$CR'R''.CHR'''CO_2H$ where R' and R'' are each hydrogen or $C_{1-4}$ alkyl and R''' is optionally substituted phenyl, —$CR'R''S(O)_nR'''$ where R' and R'' are each hydrogen or $C_{1-4}$ alkyl, R''' is optionally substituted phenyl and n is 0, 1 or 2, —$PO_3R'R''$ where R' and R'' are each hydrogen, $C_{1-4}$ alkyl or optionally substituted phenyl, —$CR'R''$—$PO_3R'''R''''$ where R', R'', R''' and R'''' are each hydrogen, $C_{1-4}$ alkyl or optionally substituted phenyl,

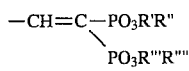

where R', R'', R''' and R'''' are each hydrogen, $C_{1-4}$ alkyl or optionally substituted phenyl,

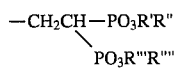

where R', R'', R''' and R'''' are each hydrogen, $C_{1-4}$ alkyl or optionally substituted phenyl, —$CH$=$NOR'$ where R' is hydrogen, $C_{1-4}$ alkyl or acyl, —$CH$=$CHR'$ where R' is —$CO_2H$, nitrile, tetrazolyl, optionally substituted benzimidazol-2-yl, optionally substituted N-$C_{1-4}$ alkyl benzimidazol2-yl, optionally substituted oxazol-5-yl or optionally substituted thiazol-5-yl, tetrazolyl, pyridyl, optionally substituted benzimidazol-2-yl, optionally substituted N-$C_{1-4}$ alkyl benzimidazol-2-yl, optionally substituted oxazol-5-yl or optionally substituted thiazol-5-yl, or —CN, and $R^4$ and $R^5$ are each hydrogen, hydroxy, nitro, $C_{1-4}$ alkyl, $C_{1-4}$ alkoxy, optionally substituted phenyl or —NR'R'' where R' and R'' are each hydrogen or $C_{1-4}$ alkyl;

provided that when $R^3$ is —$CR'R''.CHR'''CO_2H$, —CN or tetrazolyl, $R^1$ and $R^2$ are each hydroxyl, halo, $C_{1-4}$ alkyl, $C_{1-4}$ alkoxy, acyloxy, —O-glucoside or optionally substituted phenyl;

and salts and esters thereof.

Preferred groups of compounds are of the above formula (I) in which $R^1$ and $R^2$ are each hydrogen, hydroxyl, halo, $C_{1-4}$ alkyl, $C_{1-4}$ alkoxy, acyloxy, —O-glucoside, optionally substituted phenyl or optionally substituted phenyl-$C_{1-4}$ alkoxy, and $R^4$ and $R^5$ are each hydrogen, hydroxy, acyloxy, nitro, $C_{1-4}$ alkyl, $C_{1-4}$ alkoxy, halo, optionally substituted phenyl, —$SO_3H$, or —NR'R'' where R' and R'' are each hydrogen or $C_{1-4}$ alkyl, and $R^3$ is 1) —NR'S₂R" where R' is hydrogen or C₁₋₄ alkyl and R" is hydroxyl, C₁₋₄ alkyl or optionally substituted phenyl,
2) —CONR'R" where R' and R" are each hydrogen, C₁₋₄ alkyl or optionally substituted phenyl,
3) —CONR'OR" where R' is C₁₋₄ alkyl or optionally substituted phenyl and R" is C₁₋₄ alkyl or benzyl,
4) —CR'R".CR'" (NHR"")CO₂H where R' and R" are each hydrogen, C₁₋₄ alkyl or optionally substituted phenyl, R'" is hydrogen, —CO₂H or —C₁₋₄ alkylene-COOH, and R"" is hydrogen or acyl,
5) —CR'R"S(O)ₙR'" where R' and R" are each hydrogen or C₁₋₄ alkyl, R'" is optionally substituted phenyl and n is 0, 1 or 2,
6) —PO₃R'R" where R' and R" are each hydrogen, C₁₋₄ alkyl or optionally substituted phenyl,
7) —CH=CHR' where R' is —CO₂H, nitrile, tetrazolyl, optionally substituted benzimidazol-2-yl, optionally substituted N-C₁₋₄ alkyl benzimidazol-2-yl, optionally substituted oxazol-5-yl or optionally substituted thiazol-5-yl, or
8) pyridyl, optionally substituted benzimidazol-2-yl, optionally substituted N-C₁₋₄ alkyl benzimidazol-2-yl, optionally substituted oxazol-5-yl, optionally substituted oxadiazol-2-yl, and salts and esters thereof.

Compounds in which $R^3$ is tetrazolyl are particularly preferred. Thus a preferred group of compounds of formula (I) above, is one in which $R^3$ is tetrazolyl, $R^1$ and $R^2$ are each hydroxyl, halo, C₁₋₄ alkyl, C₁₋₄ alkoxy, acyloxy, —O-glucoside, optionally substituted phenyl or optionally substituted phenyl-C₁₋₄ alkoxy, and $R^4$ and $R^5$ are each hydrogen, hydroxy, acyloxy, nitro, C₁₋₄ alkyl, C₁₋₄ alkoxy, halo, optionally substituted phenyl, —SO₃H, or —NR'R" where R' and R" are each hydrogen or C₁₋₄ alkyl; and salts and esters thereof. The tetrazolyl group is attached to the nucleus via the carbon atom and can be designated tetrazol-5-yl.

When $R^3$ is tetrazolyl, a more particular group of compounds of the invention is one in which $R^1$ and $R^2$ are each hydroxyl, halo, C₁₋₄ alkyl, C₁₋₄ alkoxy, acyloxy, —O-glucoside or optionally substituted phenyl, and $R^4$ and $R^5$ are each hydrogen, hydroxy, nitro, C₁₋₄ alkyl, C₁₋₄ alkoxy, optionally substituted phenyl or —NR'R" where R' and R" are each hydrogen or C₁₋₄ alkyl. Preferably $R^1$ and $R^2$ are each hydroxyl, C₁₋₄ alkoxy or acyloxy. Preferably also $R^4$ and $R^5$ are each hydrogen, hydroxy, acyloxy, C₁₋₄ alkoxy or halo, and $R^4$ and $R^5$ are especially hydrogen.

It is preferred in all groups of compounds of formula (I) that the $R^1$ and $R^2$ positions are both substituted, that is to say, both $R^1$ and $R^2$ are other than hydrogen. Preferably $R^1$ and $R^2$ are each hydroxyl or C₁₋₄ alkoxy or acyloxy, especially acetoxy, and also $R^4$ and $R^5$ are preferably hydrogen.

Examples of novel compounds of formula (I) which are substituted in the 2-position by carboxy ($R^3$ is —CO₂H), are as follows 1) 9,10-Dihydro-9,10-dioxo-1,4,5-trihydroxyanthracene-2-carboxylic acid
2) 9,10-Dihydro-9,10-dioxo-1,4,5-triacetoxyanthracene-2-carboxylic acid
3) 9,10-Dihydro-9,10-dioxo-1,4,5,8-tetramethoxyanthracene-2-carboxylic acid
4) 9,10-Dihydro-9,10-dioxo-1,4,5,8-tetrahydroxyanthracene-2-carboxylic acid
5) 9,10-Dihydro-9,10-dioxo-1,4,5,8-tetracetoxyanthracene-2-carboxylic acid
6) 9,10-Dihydro-1,4-dimethoxy-9,10-dioxoanthracene-2-carboxylic acid
7) 1-Acetoxy-9,10-dihydro-9,10-dioxo-4-hydroxyanthracene-2-carboxylic acid
8) 9,10-Dihydro-4,5-dihydroxy-9,10-dioxo-8-fluoroanthracene-2-carboxylic acid
9) 9,10-Dihydro-4,5-dimethoxy-9,10-dioxo-8-fluoroanthracene-2-carboxylic acid
10) 9,10-Dihydro-4,5-dimethoxy-9,10-dioxo-6-fluoroanthracene-2-carboxylic acid
11) 9,10-Dihydro-4,5-dihydroxy-9,10-dioxo-6-fluoroanthracene-2-carboxylic acid
12) 3,6-Difluoro-9,10-dihydro-4,5-dimethoxy-9,10-dioxoanthracene-2 -carboxylic acid and salts and esters thereof.

In addition, the pharmaceutical uses of the above listed carboxy compounds and of the following known compounds are included in the invention 13) 9,10-Dihydro-9,10-dioxo-1,4,5-trimethoxyanthracene-2-carboxylic acid
14) 9,10-Dihydro-1,4-dihydroxy-9,10-dioxoanthracene-2-carboxylic acid
15) 1,4-Diacetoxy-9,10-dihydro-9,10-dioxoanthracene-2-carboxylic acid
16) 9,10-Dihydro-4,5-dimethoxy-9,10-dioxoanthracene-2-carboxylic acid and salts and esters thereof.

A halo group is preferably chloro, bromo or fluoro, and a C₁₋₄ alkyl group can be branched or unbranched, and for example can be methyl, ethyl, propyl, butyl or t.butyl, and is preferably methyl or ethyl. A C₁₋₄ alkoxy group is one such alkyl group linked through oxygen. An acyl group is of the formula XCO— and an acyloxy group of the formula XCO.O—, where X is preferably C₁₋₄ alkyl, acetoxy and propionyloxy being especially preferred.

An optionally substituted phenyl group is phenyl or phenyl substituted with one or more substituents, such as for example C₁₋₄ alkyl, especially methyl, C₁₋₄ alkoxy, especially methoxy and ethoxy, carboxy, hydroxy, cyano, halo trifluoromethyl, nitro, tetrazolyl and amino. Preferably there are one to three substituents and preferred values are unsubstituted phenyl or phenyl substituted with a single carboxyl, nitro, C₁₋₄ alkyl or trifluoromethyl group.

An optionally substituted phenyl-C₁₋₄ alkoxy is one such phenyl linked through a C₁₋₄ alkoxy group, preferably of the form —(CH₂)ₙO— where n is 1 to 4. A preferred group is optionally substituted benzyloxy and especially benzyloxy itself.

An optionally substituted benzimidazol-2-yl, N-C₁₋₄ alkyl benzimidazol-2-yl or oxadiazol-2-yl can be substituted by one or more substituents, preferably a single substituent, for example one of the values listed for substituted phenyl.

An optionally substituted oxazol-5-yl, thiazol-5-yl, isoxazol-5-yl, isothiazol-5-yl or isothiadazol-2-yl is preferably substituted with a single hydroxyl group. A heterocyclyl substituent is preferably tetrazolyl, benzimidazol-2-yl, N-C₁₋₄ benzimidazol-2-yl or oxadiazol-2-yl.

Compounds in which $R^3$ is —CH=CHR' and —CH=CH—PO₃R can exist as geometric isomers, and such geometric isomers and mixtures of them are included in the invention. Generally the trans form predominates. The cis isomer can be separated from mixtures by conventional means or synthesized by special methods for its preparation.

Compounds in which $R^3$ is —CR'R",CR'" (NHR"")CO₂H can exist in both R and S forms being generally obtained by the preparative methods described as mixtures. The forms can be separated by conventional methods or prepared by special methods that give one isomer exclusively.

It will also be understood that salts of the compounds of the invention can be prepared and such salts are included in the invention. They can be any of the well known base or acid addition salts. Examples of base salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example glycollic, maleic, fumaric, malic, tartaric, citric, salicylic or o-acetoxybenzoic acids, or organic sulphonic acids, methane sulphonic, 2-hydroxyethane sulphonic, toluene-p-sulphonic or naphthalene-2-sulphonic acids.

In addition to pharmaceutically-acceptable salts, other salts are included in the invention. They may serve as intermediates in the purification of compounds or in the preparation of other, for example pharmaceutically-acceptable, salts, or are useful for identification, characterisation or purification.

The compounds can also be utilised in ester form, such esters being aliphatic or aromatic. The esters principally concerned are those derived from compounds in which $R^3$ is —COOH or in which the $R^3$ group bears one or more —COOH. The most preferred esters are alkyl esters derived from $C_{1-4}$ alkanols, especially methyl and ethyl esters. Other esters that can be employed are hydroxylated esters derived from for example glycollic, malic, tartaric, citric, salicylic or 2-hydroxyethane sulphonic acids.

The invention also includes a process for producing novel compounds according to formula (I) above, which comprises:

1) converting a compound of formula (I), in which $R^3$ is —$CO_2H$ and $R^1$, $R^2$, $R^4$ and $R^5$ are as defined above, to a compound in which $R^3$ is —CONR'R" or —CONR'OR" where R' and R" are as defined above, 2) reacting a compound of formula (I), in which $R^3$ is —NHR' and $R^1$, $R^2$, $R^4$ and $R^5$ are as defined above, with a compound of formula R"$SO_2X$ (II) where X is a leaving group, to give a compound in which $R^3$ is —NR'$SO_2$R", and R' and R" are as defined above, 3) converting a compound of formula (III)

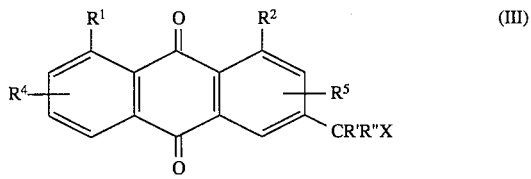

where $R^1$, $R^2$, $R^4$, $R^5$, R' and R" are as defined above and X is halo, to a compound of formula (I) in which $R^3$ is —CR'R" CH($NH_2$)$CO_2H$, —CR'R"CHR'"$CO_2H$, —CR'R"SR'", —CR'R"—$PO_3$R'"R"", or

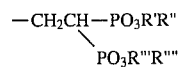

4) oxidising a compound of formula (I) in which $R^3$ is —CR'R"SR'" to give a compound in which $R^3$ is —CR'R"S(O)$_n$R'" in which R', R" and R'" are as defined above and n is 1 or 2, 5) converting a compound of formula (I) in which $R^3$ is —CHO to a compound in which $R^3$ is —CH=CHR', —CH=CH—$PO_3$R'R",

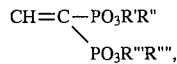

optionally substituted benzimidazol-2-yl or tetrazolyl, 6) converting a compound of formula (I) in which $R^3$ is —$NH_2$ to a compound in which $R^3$ is —$PO_3$R'R", 7) converting a compound of formula (I) in which $R^3$ is —CN to a compound in which $R^3$ is tetrazolyl, or 8) converting a $R^1$, $R^2$, $R^4$ or $R^5$ group to hydroxy, $C_{1-4}$ alkoxy or acyloxy.

As described above, a starting material in process variant (1) is the compound of formula (I) in which $R^3$ is —$CO_2H$. Compounds of this kind are either known or can be made by methods known in the art. Compounds that are readily available from commercial sources include, for example, rhein and diacetyl rhein, of formula (I) in which (1) $R^1$ and $R^2$ are hydroxyl, $R^4$ and $R^5$ are hydrogen and $R^3$ is —$CO_2H$, and (2) $R^1$ and $R^2$ are —$OCOCH_3$, $R^4$ and $R^5$ are hydrogen and $R^3$ is —$CO_2H$, respectively. Starting compounds in which $R^1$ and $R^2$ are halo can be prepared by halogenation of rhein or its analogues or if necessary when $R^1$ or $R^2$ is hydroxyl the group can be protected by an acyl group, or converted to $C_{1-4}$ alkoxy or phenylalkoxy by known means.

Thus process variant (1) comprises reacting a compound of formula (I) in which $R^3$ is —$CO_2H$ to produce a compound in which $R^3$ is —CONR'R" or —CONR'OR', by known means and under standard conditions as, for example, at a temperature of from 0° C. to 200° C., and in the presence of an organic solvent. In the case of compounds in which $R^3$ is —CONR'R" the intermediate of formula (I) in which $R^3$ is $CO_2H$ can be reacted with a suitable amine of formula HNR'R". In the case of compounds in which $R^3$ is —CONR'OR" the intermediate can be reacted with a compound of the formula HNR'OR", such hydroxylamine derivatives being well known in the art.

With regard to process variant (2), the reaction of a compound of formula (I) in which $R^3$ is —NHR' with R"$SO_2X$ yields compounds of formula (I) in which $R^3$ is —NR'$SO_2$R". The group X is a leaving group such as, for example, halo, especially chloro or bromo. The reaction is of a standard type and generally temperatures of from –50° C. to 100° C. are employed and an organic solvent. The intermediate compound in which $R^3$ is NHR' can be prepared from the corresponding carboxyl derivative via an isocyanate to give the free amine in which $R^3$ is —$NH_2$, which can then be alkylated.

With regard to compounds of formula (III), employed in process variant (3), these can be prepared from compounds of formula:

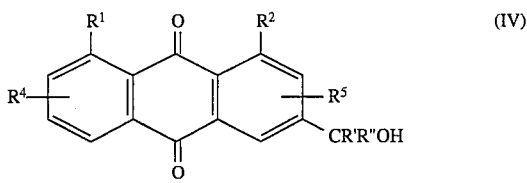

The compound of formula (IV) above, in which $R^1$ and $R^2$ are hydroxyl and $R^4$, $R^5$, R' and R" are hydrogen is commercially available as aloe-emodin, and other starting materials of formula (IV) can be made by standard procedures, the R' and R" groups, when other than hydrogen, being introduced by alkylation. Preferably such hydroxy groups in the intermediate are alkylated to the alkoxy form, prior to reaction. The compounds of formula (III) can be derived from those of formula (IV) by halogenation using a conventional halogenating agent such as phosphorus pentachloride.

The compound of formula (III) can be reacted with a malonate reactant of the formula $YNHCH(CO_2R)_2$ where Y is a conventional amino-protecting group and R is an ester forming group preferably $C_{1-4}$ alkyl, or of the formula $R'''CH(CO_2R)_2$ where R is an ester forming group preferably $C_{1-4}$ alkyl, to yield compounds in which $R^3$ is —CR'R"CH(NH$_2$)CO$_2$H or —CR'R"CHR'''CO$_2$H, respectively. The reaction is preferably carried out on at a temperature of from 0° C. to 200° C. under hydrolytic and decarboxylating conditions.

When $R^3$ is —CR'R"SR''', the thio derivative can be prepared by reaction of a compound of formula (III) with the appropriate mercaptan of formula R'''SH. The reaction is preferably carried out at a temperature of from −50° C. to 100° C., in an organic solvent such as for example dimethylformamide.

When $R^3$ is a methylene or vinyl phosphonic acid derivative it can be prepared by use of the reaction of the appropriate phosphorus reagent such

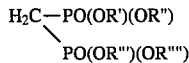

With regard to process variant (4), the sulphide compounds of formula (I) in which $R^3$ is —CR'R"SR''' can be oxidised to give compounds in which $R^3$ is —CR'R"S(O)$_n$R''' where n is 1 or 2, by use of a conventional oxidising agent employing suitable quantities to give either the sulphoxide (n is 1) or sulphone (n is 2).

With regard to process variant (5), acrylic derivatives ($R^3$ is —CH=CHR') can be prepared from the corresponding aldehydo derivative by reaction with the appropriate stabilised ylid or activated methylene compound such as malonic acid, under standard conditions at a temperature of from −50° C. to 150° C. Similar oxidising agents and conditions can be used to convert known derivatives of formula (III) in which $R^3$ is —CH$_2$OH to the aldehydo intermediate, as those described for process variant (4).

With regard to process variant (6), compounds in which $R^3$ is —PO$_3$R'R" can be prepared by diazotisation of the amine ($R^3$ is —NH$_2$) and reaction with the appropriate hypophosphite.

With regard to process variant (7), the tetrazolyl derivative can be prepared from a compound of formula (I) in which $R^3$ is —CN by reaction with metal azide, for example sodium azide, preferably in an organic solvent such as, for example, dimethylformamide, and at a temperature of from 0° C. to 200° C. The nitrile intermediate can in its turn be prepared from the corresponding aldoxime ($R^3$ is —CH=NOH) by dehydration using trifluoroacetic anhydride.

It will be appreciated that conventional means of hydrolysis, alkylation or acylation can be performed on compounds with appropriate values of $R^1$, $R^2$, $R^3$ and $R^4$, or for example by alkylation of benzimidazol-2-yl to give a N-alkylated derivative. When $R^4$ or $R^5$ is —SO$_3$H the compound can be prepared by reaction of the nucleus with sulphuric acid.

Osteoarthritis and allied connective tissue matrix diseases such as, for example, osteoporosis and rheumatoid arthritis, are often characterised by an increase in matrix synthesis and remodelling. Incorporation of newly synthesized components into a biological and biomechanically functional matrix is, however, frequently deficient. Drugs which modulate the activity of the cells involved in such connective tissue matrix maintenance and repair are, therefore, of potential use in such diseases.

The compounds produce dose-dependent inhibition of in vitro tumour cell proliferation with IC50 values ranging from 1–50 μM. Partial inhibitory effects of around 30% were also observed for several compounds on tumour cell protein synthesis at a concentration of 100 μM using a method similar to that described by A. Floridi et al, Exp. Mol. Pathol., 1985, 42, 293–305. The majority of the compounds also inhibited mitogen-induced lymphocyte proliferation with IC50 values ranging from 10–100 μM.

Further modulatory effects of the compounds were observed in an in vitro model system used to study the differentiation of chondrocytes from prechondrogenic stem cells, as described by D. F. Paulsen et al, In Vitro Cellular and Developmental Biology 24, 138–147. The compounds demonstrate bimodal concentration effects on the production of matrix components by differentiating chick limb bud chondrocytes. Inhibitory effects of up to 95% were observed at concentrations ranging from 10–100 μM whereas at submicromolar concentrations the compounds produced up to a three-fold stimulation in the synthesis of matrix macromolecules.

Further evidence of activity has been provided by studying the effect of compounds of the invention on lesions in guinea pigs. Spontaneous lesions of osteoarthritis were first described in the hind knee joints of old guinea pigs by Silverstein and Sokoloff (Arthritis Rheum. 1, 82–86 (1958)). Bendele and Hulman (Arthritis Rheum. 31, 561–565 (1988)) and Bendele, White and Hulman (Lab. Anim. Sci. 39, 115–121 (1989)) studied younger animals and were the first to describe the time course of progressing osteoarthritis in outbred male guinea pigs. These latter studies were confirmed and extended by Meacock, Bodmer and Billingham (J. Exp. Path. 71, 279–293 (1990)), also in outbred male guinea pigs.

It has been possible to devise a scoring system based on the severity of lesions on the medial tibial plateau and medial femoral condyle (i.e. 0=normal, 15=total loss of cartilage) and on the number of osteophytes present (i.e. 0–4), and to use this to assess drug activity in an in vivo screen in which test compounds are administered daily and orally to groups of 3 month-old guinea pigs for 3 and 6 months. Histological sections are prepared at 6 levels in each joint, stained and scored blind. After decoding the average scores of the 12 sections from each animal are analysed statistically by analysis of variance and activity is recognised if $p<0.05$. The activity of compounds has been confirmed in this test.

The compounds of the invention are thus particularly indicated for use in the treatment of osteoarthritis and allied connective tissue matrix diseases such as, for example, osteoporosis and rheumatoid arthritis. Furthermore, the inhibitory properties on tumour cell proliferation indicate that the compounds are of potential in the treatment of cancer.

The invention also includes a pharmaceutical composition comprising a pharmaceutically acceptable diluent or carrier in association with a compound of the invention, or a pharmaceutically acceptable salt or ester thereof.

The compounds may be administered by various routes, for example by the oral or rectal route, topically or parenterally, for example by injection or infusion, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing, for example, up to 10% by weight of the compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydrobenzoate, talc magnesium stearate and mineral oil. The compositions of an injection may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example from 25 mg to 200 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the conditions to be treated, the choice of compound to be administered and the chosen route of administration, and therefore the above dosage ranges are not intended to limit the scope of the invention in any way.

The invention is illustrated by the following Examples.

EXAMPLE 1

1) 9,10-Dihydro-4,5-dihydroxy-9,10-dioxoanthracene-2-carboxylic acid 4,5-Diacetoxy-9,10-dihydro-9,10-dioxoanthracene-2-carboxylic acid (5 g) was magnetically stirred in 5% w/v aqueous sodium carbonate (100 ml) at 80° C. for 2 hours 25 minutes.

The suspension was allowed to cool, then diluted with water (100 ml) and adjusted to pH 1 by addition of concentrated hydrochloric acid. After filtering and washing with water (200 ml), the collected yellow-brown solid was dried at 64° C. in vacuo, m.p. >260° C.

2) Methyl 9,10-dihydro-4,5-dimethoxy-9,10-dioxoanthracene-2-carboxylate

A mixture of 9,10-dihydro-4,5-dihydroxy-9,10-dioxoanthracene-2-carboxylic acid (28.4 g), dimethyl sulphate (59 ml; 79 g) and anhydrous potassium carbonate (207 g) in 'Drierire' dried acetone (1350 ml) and dioxan (1200 ml) was heated at reflux for 17 hours, with mechanical stirring. After allowing to cool, the suspension was filtered and the filter contents were washed with hot dioxan (5×50 ml).

The combined filtrate and washings deposited a yellow solid on standing. The solid was removed by filtration and washed with 40–60 petrol (2×100 ml). After drying at 45° C. in vacuo the pure solid weighed 13.24 g, m.p. 211°–212° C.

A further batch of pure carboxylate was obtained from the filtrate by evaporation, then stirring the yellow residual solid in water (200 ml). The product was filtered, washed with water (50 ml) and dried at 73° C. in vacuo.

3) 9,10-Dihydro-4,5-dimetho-9,10-dioxoanthracene-2-qaboxylic acid

Methyl 9,10-dihydro-4,5-dimethoxy-9,10-dioxoanthracene-2-carboxylate (10 g) and crushed sodium hydroxide pellets (3.675 g) were magnetically stirred at room temperature for 19.5 hours in dioxan (100 ml) and water (25 ml).

The suspension was evaporated to dryness in vacuo to leave a yellow-brown solid, which was then dissolved in water (100 ml) and adjusted to pH 1 by addition of concentrated hydrochloric acid. After stirring with acetone (50 ml), the mixture was filtered to remove a mustard coloured solid. This was washed with acetone (50 ml) and dried at 70° C. in vacuo.

The solid was stirred in hot dioxan (600 ml) then filtered hot to remove a little insoluble solid which was washed on the filter with hot dioxan (150 ml). The filtrate and washings were combined and allowed to stand over night at room temperature, during which time a yellow crystalline solid separated.

The pure acid was removed by filtration, washed with acetone (50 ml) then dried at 98° C. in vacuo, m.p. 288°–289° C.

EXAMPLE 2

1) 9,10-Dihydro-4,5dimethoxy-9,10dioxo-2-hydroxymethyl-anthracene 9,10-Dihydro-4,5-dihydroxy-9,10-dioxo-2-hydroxymethyl-anthracene (aloe-emodin) (45 g) and anhydrous potassium carbonate (225 g) were mechanically stirred in 'Drierire' dried acetone (2.5 l) and 'Drierite' dried dioxan (1l) before adding dimethyl sulphate (67.5 ml; 89.8 g). The mixture was heated at reflux for 20.5 hours.

The resulting mustard coloured suspension was cooled, then filtered to remove solids, which were then washed on the filter with hot acetone (5×250 ml). The contents of the filter were stirred in water (3 l) for 15 minutes, filtered, washed with water, (3×500 ml) and dried at 110° C. in vacuo to leave the pure dimethoxy compound, m.p. 230° C.

2) 9,10-Dihydro-4,5-dimethoxy-9,10-dioxonthracene-2-carboxaldehyde

A solution of sulphur trioxide pyridine complex (136.73 g) in 4H molecular sieve dried DMSO (360 ml) was added, from a dropping funnel, during 10 minutes with mechanical stirring, to a suspension of 9,10 -dihydro-4,5-dimethoxy-9,10-dioxo-2-hydroxymethyl-anthracene (25.75 g) in dry DMSO (250 ml) and triethylamine (360 ml).

The reaction mixture became warm and darkened. Stirring was continued for 17 hours at ambient temperature, during which time a light brown solid separated.

The mixture was poured into 0.5N hydrochloric acid (6 1), stirred, then left for 15 minutes before filtering. The mustard coloured solid on the filter was washed with water (4 1) then dried at 70° C. in vacuo, to leave the pure carboxaldehyde, m.p. 235°–236° C.

EXAMPLE 3

2- 1H-Benzimidazol-2-vl)-9,10-dihydro-4,5-dimethoxy-9,10-dioxoanthracene

A suspension of 9,10-dihydro-4,5-dimethoxy-9,10-dioxoanthracene-2 -carboxaldehyde (3 g) and sodium metabisulphite (0.95 g) in absolute ethanol (60 ml) and water (12 ml) was heated on a steam bath, with hand swirling, to effect almost complete solution.

Evaporation at 55° C. in vacuo left a yellow-brown solid, to which was added a solution of o-phenylenediamine (1.04 g) in 1-methyl-2-pyrrolidinone (30 ml). After magnetically stirring for 2 hours at 120° C. under nitrogen, the brown solution was allowed to cool, then poured on to crushed ice (approximately 400 ml). Water (100 ml) was added and the suspension was stirred for 30 minutes before filtering. The brown solid retained on the filter was washed with water (400 ml) then dried at 110° C. in vacuo.

The crude benzimidazole, together with decolourising charcoal (2 g), was stirred in boiling dioxan (600 ml) for 10 minutes. The charcoal was removed by filtering, hot, through 'Hyflo'. The contents of the filter were washed with hot dioxan (150 ml), and the filtrate and washings were combined and evaporated in vacuo to leave a yellowy brown solid. After crystallisation from absolute ethanol (100 ml) a yellowy tan coloured crystalline solid was obtained. Drying at 120° C. in vacuo left the pure benzimidazole, m.p. 275°–276° C.

EXAMPLE 4

2-(1H-Benzimidazol-2-yl)-9,10-dihydro-9,10-dioxo-5-hydroxy-4-methoxyanthracene 2-(1H-Benzimidazol-2-yl)-9,10-dihydro-4,5-dimethoxy-9,10-dioxoanthracene (3.36 g) was suspended in 4.1M hydrobromic acid in acetic acid (250 ml) and magnetically stirred under reflux for 20 hours.

The resulting cream coloured suspension was poured into water (1.5 1), stirred, then filtered to remove the crude mono hydroxyanthracene. After washing with water (500 ml) and drying at 110° C. in vacuo, the light brown solid was charcoaled (0.17 g) in boiling pyridine (30 ml). The charcoal was removed by filtration from the hot solution and washed with hot pyridine (2×5 ml). The filtrate and washings were combined and stood at room temperature for 2 hours 40 minutes, during which time a reddish-brown solid separated. The solid was removed by filtration, followed by washing with absolute ethanol (5 ml), water (2×25 ml), then ethanol (2×ml) and drying at 110° C. in vdcuo, m.p. 295°–297° C.

EXAMPLE 5

2-(1H-Benzimidazol-2-yl)-9,10-dihydro-4,5-dihydroxy-9,10-dioxoanthracene

A mixture of 2-(1H-benzimidazol-2-yl)-9,10-dihydro-4,5-dimethoxy-9,10 -dioxoanthracene (0.4 g) and freshly dried lithium iodide (0.474 g) in dry pyridine (2 ml) and sym. collidine (2 ml) was magnetically stirred and heated under reflux for 20 hours.

The purple coloured reaction mixture was allowed to cool, then poured into water (150 ml) and stirred. Concentrated hydrochloric acid was carefully added to adjust to pH 1.

A tan coloured solid was removed by filtration and washed on the filter with water (200 ml). After drying at 110° C. in vacuo slightly impure 2-(1H-benzimidazol- 2-yl)-9,10-dihydro-4,5-dihydroxy-9,10-dioxoanthracene was obtained.

Purification was effected by crystallisation from slightly aqueous 1-methyl-2-pyrrolidinone, m.p. >310° C.

EXAMPLE 6

1) 9,10-Dihydro-4,5-dihydroxy-9,10-dioxoanthracene-2-aldehyde

To aloe-emodin (5.0 g) in dry dimethyl sulphoxide (55 ml) and triethylamine (77 ml) was added a solution/suspension of sulphur trioxide-pyridine complex (29.4 g) in dry dimethyl sulphoxide (100 ml), dropwise with stirring, over 15 minutes. The addition was slightly exothermic and gave a dark brown solution, which was stirred at room temperature for 2–3 hours, then poured onto dilute hydrochloric acid (1000 ml, 0.5M), stirred for 15 minutes, then left to stand for 15 minutes. The suspension was filtered (slow), washed with water (400 ml) and pulled dry to leave a brown solid. Dried at 50° C. in a vacuum oven, m.p. 198°–200° C.

2-(1H-Benzimiazol-2-yl)-9,10-dihydroxy-4,5-dihydroxy-9,10-dioxoanthraguinone

To a partial solution of 4,5-tihydroxyanthraquinone-2-aldehyde (4.0 g) in 1,4-dioxan (100 ml), heated on a team bath, with swirling, was added an aqueous (30 ml) solution of sodium metabisulphite (1.56 g) The solution thickened and was heated with swirling for 30 minutes, allowed to cool to room temperature, filtered and the filter pad washed with acetone (50 ml) to give a dark brown solid. Dried at 50° C. in a vacuum oven. The bisulphite adduct and o-phenylenediamine (0.95 g) were then dissolved in 1-methylpyrrolidin-2-one (30 ml) and heated with stirring at 100° C. for 4 hours. The suspension was then poured onto ice (500 ml)/water (100 ml), stirred for 10 minutes, allowed to stand for 30 minutes and filtered (slow) to give a brown solid. Dried at 50° C. in a vacuum oven, m.p. >300° C.

3) (1H-Benzimidazol-2-yl)-4,5-dicetoxy-9,10-dihydro-9,10-dioxoanthrancen

To 2-(1H-benzimidazol-2-yl)-9,10-dihydro-4,5-dihydroxy-9,10-dioxoanthracene (1.9 g) was added concentrated sulphuric acid (3.0 g), making sure all the solid was 'wetted' with acid. Acetic anhydride (60 ml) was then added with swirling and the brown solution stirred at room temperature under nitrogen for 2 hours, filtered and washed with water (200 ml) to give a yellow-brown solid. Dried at 50° C. in a vacuum oven, m.p. >300° C.

EXAMPLE 7

9,10-Dihydro-4,5-dimethoxy-9,10-dioxo-2-(1-methyl-1H-benzimidazol-2yl-anthracene 2-(1H-Benzimidazol-2-yl)-9,10-dihydro-4,5-dimethoxy-9,10-dioxoanthracene (0.4 g) was dissolved by magnetically stirring in dry D.M.F. (10 ml).

A 50% w/w dispersion of sodium hydride in mineral oil (0.077 g) was added and the mixture was allowed to stir at room temperature for 37 minutes before adding iodomethane (0.25 ml). Stirring was continued for 23 hours. The resulting cream coloured suspension was poured into water (100 ml).

After filtration, washing on the filter with water (3×50 ml), then 40°–60° C. petroleum ether (2×50 ml) and drying at 110° C. in vacuo, 9,10 -dihydro-4,5-dimethoxy-9,10-dioxo-2-(1-methyl-1H-benzimidazol-2-yl)anthracene was obtained, m.p. 283°–284° C.

EXAMPLE 8

9,10-Dihydro-4,5-dihydroxy-2-(1-methyl-1H-benzimidazol-2-yl)-9,10-dioxoanthracene A suspension of 9,10-dihydro-4,5-dimethoxy-2-(1-methyl-1H-benzimidazol-2 -yl)-9,10-dioxoanthracene (0.31 g) and anhydrous lithium iodide (0.26 g) in N-methyl piperidine (2 ml) and 2,4,6-collidine (2 ml) was magnetically stirred under reflux for 19.5 hours.

The purple coloured reaction mixture was allowed to cool to room temperature, then poured into water (75 ml). Concentrated hydrochloric acid, followed by glacial acetic acid, was added to adjust to pH 3.

The resulting tan coloured solid precipitate was removed by filtration, washed on the filter with water (100 ml), followed by ethanol (10 ml), then dried at 110° C. in vacuo to give 0.28 g of slightly impure required product.

This solid (0.134 g) was stirred in a boiling mixture of chloroform (10 ml) and methanol (20 ml) for 5 minutes. After standing for 45 minutes at room temperature, then filtering and drying at 80° C. in vacuo, pure 9,10-dihydro-4,5-dihydroxy-2-(1-methyl-1H-benzimidazol-2-yl)-9,10-dioxoanthracene was obtained as a cream coloured solid, m.p. 266°–267° C.

EXAMPLE 9

4,5-Diactoxy-9,10-dihydro-2-(1-methyl-1H-benzimidazol-2-yl)-9,10-dioxoanthracene 9,10-Dihydro-4,5-dihydroxy-2-(1-methyl-1H-benzimidazol-2-yl)-9,10dioxoanthracene (0.072 g) was wetted with concentrated sulphuric acid (6 drops) by stirring, magnetically, for 5 minutes.

Acetic anhydride (2 ml) was added and stirring was continued for a further 7.5 hours, then allowed to stand overnight.

The resulting clear solution was diluted with water (10 ml) and after stirring for 30 minutes a yellow solid was removed by filtration, washed with water (25 ml) and dried at 75° C. in vacuo to give pure 4,5-diacetoxy-9,10 -dihydro-2-(1-methyl-1H-benzimidazol-2-yl)-9,10-dioxoanthracene, m.p. 279°–280° C.

EXAMPLE 10

2-(1H-Benzimidazol-2-yl)-4,5-diacetoxy-9,10-dihydro-9,10-dioxoanthracene methane sulphonic acid salt A solution of methane sulphonic acid (0.09 g) in dioxan (2 ml) was added to a solution of 2-(1H-benzimidazol-2-yl)-4,5-diacetoxy-9,10-dihydro-9,10-dioxoanthracene (0.124 g) in dioxan (5 ml). Within 1 minute a light brown solid began to crystallise.

After 1.5 hours the light brown crystalline acid salt was removed by filtration, washed with diethyl ether (25 ml), then dried at 60° C. in vacuo, m.p. >310° C., previous softening at 160° C.

EXAMPLE 11

2-(1H-Benzimidazol-2-yl)-4,5-diacetoxy-9,10-dihydro-9,10-dioxoanthracene hydrochloride salt A 1 molar solution of methanolic hydrogen chloride (10 ml) was added to a solution of 2-(1H-benzimidazol-2-yl)-4,5-diacetoxy-9,10-dihydro-9,10-dioxoanthracene (0.045 g).

The solution was evaporated at 54° C. in vacuo to leave the hydrochloric salt, which was dried at 65° C. in vacuo.

EXAMPLE 12

9,10-Dihydro-4,5-dimethoxy-9,10-dioxoanthracene-2-aldoximine

Hydroxylamine hydrochloride (2.432 g) was added to 9,10-dihydro-4,5 -dimethoxy-9,10-dioxoanthracene-2-carboxaldehyde (10 g) and pyridine (10 ml) in dioxan (100 ml) and then heated under reflux under nitrogen with mechanical stirring for 16 hours, filtered and washed with diethyl ether (100 ml), then dried in vacuo at 65° C. for 24 hours to give the oxime, m.p. 254°–256° C.

EXAMPLE 13

9,10-Dihydro-4,5-dimethoxy-9,10-dioxoanthracene-2-carbonitrile

Trifluoroacetic anhydride (4.62 ml, 6.87 g), was added dropwise with magnetic stirring to a suspension of 9,10-dihydro-4,5-dimethoxy-9,10 -dioxoanthracene-2-aldoxime (10.74 ml, 9.24 g) in pyridine (10.5 ml, 10.336 g) and dioxan (100 ml) at room temperature under nitrogen. The temperature rose from 23° C. to 31° C. The mixture was then heated at 65° C. for 2 hours. More trifluoroacetic anhydride (4.62 ml, 6.87 g) was added at 65° C. and the mixture was stirred for a further 1 hour at 65° C. More trifluoroacetic acid (1 ml, 1.487 g) was added and the mixture stirred for 16 hours at 65° C., cooled, filtered, washed with water (200 ml) and dried in vacuo at 70° C. to give the nitrile, m.p. 266°–268° C.

EXAMPLE 14

5-(9,10-Dihydro-4,5-dimethoxy-9,10-dioxoanthracen-2-yl)tetrazole

Tri-n-butyltin azide (100 ml) was added to 9,10-dihydro-4,5-dimethoxy-9,10 -dioxoanthracene-2-carbonitrile (5.75 g) and heated and stirred at 150° C. for 4 hours, cooled to room temperature, poured into ethyl acetate (1000 ml). Acetic acid (10 cm$^3$) was added and the solution allowed to stand 16 hours, the resultant precipitate was filtered to give the dimethoxyetrazole, m.p. 262°–264° C.

EXAMPLE 15

5-(9,10-Dihydro-4,5-dihydroxy-9,10-dioxoanthracen-2-yl)tetrazole

33% Hydrobromic acid in glacial acetic acid (200 ml) was added to 5-(4,5 -dimethoxy-9,10-dihydro-9,10-dioxoanthracen-2-yl)tetrazole (4 g) and the mixture heated and stirred at 100° C. under nitrogen for 16 hours, cooled to room temperature, filtered, washed with water and dried in vacuo to give the dihydroxytetrazole, m.p. 262° C. (dec.)

EXAMPLE 16

4,5-Diacetoxy-9,10-dihydro-N-(1,1-dimethylethyl)-9,10-dioxoanthracene-2-carboxamide To a stirred mixture of 4,5-diacetoxy-9,10-dihydro-9,10-dioxoanthracene-2 -carboxylic acid and thionyl chloride (3.6 liters) was added dry pyridine (267.0 ml) dropwise over 15 minutes. The mixture was heated under reflux for 4 hours and then cooled to 40° C. The excess thionyl chloride was removed by distillation in vacuo and replaced with toluene (6 liters). The mixture was cooled to 15° C. and tert-butylamine (600 ml) was added over 10 minutes. The mixture was left to stir at room temperature over-night. More tert-butylamine (550 ml) was added (550 ml) was added until no more starting material could be detected. The mixture was cooled to 0°–5° C. and the solid isolated by

EXAMPLE 17

4,5-Diacetoxy-9,10-dihydro-9,10-dioxoanthracene-2-carbonitrile

A stirred mixture of 4,5-diacetoxy-9,10-dihydro-N-(1,1-dimethylethyl)-9,10-dioxoanthracene-2-carboxamide (337.0 g) and toluene was warmed to 105° C. and then filtered through a pre-warmed glass sinter funnel. The stirred filtrate was heated back to 100° C. and phosphorus pentachloride (278.0 g) was added portionwise over 15 minutes. The heat was removed and the mixture allowed to cool to room temperature. The mixture was cooled further to 15° C. and the material isolated by filtration and washed in turn with toluene, aqueous sodium bicarbonate (1.5 liters) and water (2×1.5 liters). The green solid was then dried in vacuo at 45° C., m.p. 218°–220° C.

EXAMPLE 18

5-(9,10-Dihydro-4,5-dihydroxy-9,10-dioxoanthracen-2-yl)tetrazole

A stirred mixture of 4,5-diacetoxy-9,10-dihydro-9,10-dioxoanthracene-2 -carbonitrile (31.4 g), D.M.F. (750 ml), sodium azide (20.4 g) and triethylamine hydrochloride (44.0 g), under a nitrogen purge, was heated at 110°–115° C. for 3 hours and at 125°–130° C. for a further 4 hours. The heat was removed and the mixture cooled to room temperature. The mother liquor was decanted from some solid residue and the volatiles were removed in vacuo. The residue was quenched with dilute hydrochloric acid (33 ml conc. hydrochloric acid in 1.1 liters of water). The solid produced was isolated by filtration, washed with water and dried in vacuo at 50° C.

The dark brown material was ground to a fine powder and slurried in 1,4-dioxan (3.5 liters) for 30 minutes. The slurry was filtered through a pad of Celite and the filtrate stirred with decolorising charcoal (7 g) for 10 minutes. The slurry was again filtered through a pad of Celite and the filtrate concentrated to dryness in vacuo. The residue was triturated with dichloromethane (700 ml) and then isolated and dried in vacuo at 50° C., m.p. 242°–244° C.

EXAMPLE 19

5-(4,5-Diacetoxy-9,10-dihydro-9,10-dioxoanthracen-2-yl)tetrazole 5-(9,10-Dihydro-4,5-dihydroxy-9,10-dioxoanthracen-2-yl)tetrazole (160.0 g) was coated with concentrated sulphuric acid (300 g) and then acetic anhydride (6 liters) added. The mixture was stirred under a nitrogen purge at room temperature for 3 hours. The solid present was isolated by filtration and pulled dry. The isolated solid was then slurried in ice for 10 minutes. The material was re-isolated, washed with water and then pulled dry. The yellow/green solid was then dried in vdcuo at 25° C., m.p. 189°–190° C.

EXAMPLE 20

5-(9,10-Dihydro-9,10-dipropionyloxyanthracen-2-yl)tetrazole 5-(9,10-Dihydro-4,5-dihydroxy-9,10-dioxoanthracen-2-yl)tetrazole (0.308 g) was suspended in propionic anhydride (5.6 ml) and anhydrous pyridine (0.34 ml). The mixture was stirred and heated under reflux for 3 hours 20 minutes, then evaporated in vacuo.

The residue was stirred in ether (25 ml), then filtered to remove a cream coloured solid which was stirred and heated under reflux in dioxan (5 ml) and water (1.5 ml) for 1 hour 5 minutes.

After standing at room temperature overnight, water (5 ml) was added with stirring, before filtering to remove the solid. After drying at 80° C. in vacuo, then recrystallising from isopropyl alcohol, filtering and drying at 75° C. in vacuo, 5-(9,10-dihydro-9,10-dioxo-4,5 -dipropionyloxyanthracen-2-yl)tetrazole was obtained, m.p. 176°–178° C.—partial at 100° C.

EXAMPLE 21

1-(4,5-Diacetoxy-9,10-dihydro-9,10-dioxonthracen-2-yl)-5-methyl-1,3,4-oxadiazole Acetic anhydride (160 ml) was added to 5-(4,5-diacetoxy-9,10-dihydro-9,10 -dioxoanthracen-2-yl)-tetrazole (3.92 g) and heated and stirred under reflux under nitrogen for 1 hour, cooled, poured into water (1200 ml), and stirred for 30 minutes and the precipitated solid was removed by filtration, washed with water (300 ml) and dried in vacuo at 70° C. to give a yellow solid (3.57 g), m.p. 230°–232° C. (toluene).

EXAMPLE 22

1-(9,10-Dihydro-4,5-dihydroxy-9,10-dioxoanthracen-2-yl)-5-methyl-1,3,4 -oxadiazole Lithium hydroxide monohydrate (0.168 g) was added to a mixture of 1-(4,5 -diacetoxy-9,10-dihydro-9,10-dioxoanthracen-2-yl)-5-methyl-1,3,4-oxadiazole (0.20 g) in THF (9 ml) and water (9 ml) and stirred for 24 hours at room temperature, acidified with hydrochloric acid (2M, 4 ml). The precipitated solid was removed by filtration, washed with water and dried in vacuo at 70° C. to give a yellow solid, m.p. 252°–254° C.

EXAMPLE 23

1) Bromomethyl-9,10-dihydro-4,5-dihydroxy-9,10-dioxoanthracene

48% Hydrobromic acid (350 ml) was added to 9,10-dihydro-4,5-dihydroxy-2 -hydroxymethyl-9,10-dioxoanthracene (20 g) and heated and mechanically stirred under reflux for 4 hours, cooled, filtered, washed with water (3×80 ml), dried in vacuo at 40° C. to give bromomethyl-9,10-dihydro-9,10-dioxoanthracene (Method of J. Org. Chem., 1980, 45, 20.), m.p. 219°–220° C.

2) Ethyl 2-acetamido-2-carboxyethyl-3-(9,10-dihydro-4,5-dihydroxy-9,10 -dioxoanthracen-2-yl)propionate Diethyl acetamidomalonate (1.975 g) was added in portions to hexane washed sodium hydride in oil (60%, 0.24 g) in dry dimethylformamide (60 ml). The mixture was stirred for 1 hour at room temperature, then 2-bromomethyl-9,10-dihydro-4,5-dihydroxy-9,10-dioxoanthracene (1 g) suspended in dry dimethylformamide (20 ml) was added and the violet solution stirred for 1 hour at room temperature, poured into water (300 ml) containing hydrochloric acid (2 mol $dm^{-3}$, 50 ml), the orange precipitate filtered and dried in vacuo to give the acetamidomalonate, m.p. 190°–192° C.

EXAMPLE 24

Ethyl 2-acetamido-2-carboxyethyl-3-(9,10-dihydro-4,5-dihydroxy-9,10 -dioxoanthracen-2-yl)proprionate To a suspension of sodium hydride (23.2 g, 50% oil dispersion) in 1-methylpyrrolidin-2-one (500 ml) under nitrogen at 0°–10° C., was added a solution of diethylacetamidomalonate (113.5 g) in 1-methylpyrrolidin-2-one (1000 ml) over 45 minutes (CARE excessive foaming). The suspension was then stirred at 0°–10° C. for 90 minutes and a solution of 2-bromomethyl-9,10 -dihydro-4,5-dihydroxy-9,10-dioxoanthracene (58 g) in 1-methylpyrrolidin-2 -one (1000 ml) was added over 20 minutes to give a deep purple solution. The reaction mixture was stirred for 2 hours at room temperature, and poured onto water (5000 ml) containing hydrochloric acid (500 ml, 2N). The suspension was filtered and pulled dry to give a deep red solid. The red solid was heated at reflux with mechanical stirring in isopropanol (3500 ml) until dissolution was complete, allowed to cool to room temperature, then filtered to give a bright red solid. Dried at 50° C. in a vacuum, m.p. 189°–190° C.

EXAMPLE 25

2-Amino-3-(9,10-dihydro-4,5-dihydroxy-9,10-dioxoanthracen-2-yl)propanoic acid

A mixture of ethyl 2-acetamido-2-carboethoxy-3-(9,10-dihydro-4,5-dihydroxy-9,10-dioxoanthracen-2-yl)propanoate (99.7 g) and 47% hydrobromic acid (1500 ml) was stirred at reflux for 6 hours. The mixture was cooled to room temperature and filtered. The isolated solid was stirred with 1N sodium hdroxide (1600 ml) for 15 minutes and the mixture filtered. The filtrate was cooled to 10° C. and acidified using glacial acetic acid (720 ml). The mixture was stirred for 10 minutes and then filtered. The isolated solid was washed with water (1 liter), pulled dry and then dried in vacuo at 60° C., m.p. 210°–212° C.

EXAMPLE 26

2-Acetamido-3-(4,5-diacetoxy-9,10-dihydro-9,10-dioxoanthrcen-2-yl)propanoic acid Finely ground 2-amino-3-(9,10-dihydro-4,5-dihydroxy-9,10-dioxoanthracen-2-yl)propanoic acid (60.0 g) was coated with concentrated sulphuric acid (50.0 g) and then acetic anhydride (1800 ml) added. The mixture was stirred at room temperature for 3 hours with a nitrogen purge. After this time the mixture was filtered through a sintered glass funnel and the filtrate poured onto ice/water (3 liters). The mixture was stirred for 15 minutes and then ethyl acetate (2 liters) was added and the stirring continued for a further 10 minutes. The phases were separated and the aqueous layer extracted with more ethyl acetate (2×1 liter). The organic extracts were bulked together, washed with brine (2×2 liters) and dried over magnesium sulphate. Filtration, followed by concentration to dryness in vacuo, yielded a yellow solid. This material was triturated with water and then isolated by filtration and dried in vacuo at 60° C.

The ground solid was slurried in 5% glacial acetic acid in water (500 ml) for 2 hours at room temperature. The solid was isolated, washed with water and dried in vacuo at 60° C. The solid was then slurried in a diethyl ether (600 ml)/acetone (30 ml) mixture for 30 minutes. The material was isolated by filtration, washed with ether and dried in vacuo at 60° C., m.p. 200°–202° C.

EXAMPLE 27

2-(9,10-Dihydro-4,5-dimethoxy-9,10-dioxoanthracen-2-yl)methylthiobenzoic acid

Thiosalicylic acid (1.388 g) in dry dimethylformamide (70 ml) was added in portions to hexane washed sodium hydride in oil (60%, 0.432 g) in dimethylformamide (70 ml). The mixture was stirred for 1 hour at room temperature, then 2-bromomethyl-9,10-dihydro-4,5-dihydroxy-9,10-dioxoanthracene (3 g) was added in portions and then stirred for 16 hours at room temperature, poured into water (1400 ml) containing hydrochloric acid (2 mol $dm^{-3}$, 100 ml). The precipitated orange solid was filtered and dried to give the product, m.p. 235°–237° C.

EXAMPLE 28

1) 9-10-Dihydro-4,5-dimethoxy-9,10-dioxoanthracene-2-carbonyl azide 9,10-Dihydro-4,5-dimethoxy-9,10-dioxoanthracene-2-carboxylic acid (10 g) was suspended in dry DMF (130 ml) and cooled to 0° C. Triethylamine (3.89 g) was then carefully added, followed by a solution of diphenylphosphoryl azide (10.57 g) in dry DMF (20 ml). A yellow precipitate was generated during 12 hours stirring at room temperature. The precipitate was collected by filtration and washed with saturated sodium bicarbonate solution (1×100 ml) and water (5×100 ml). Drying in vacuo over silica gel yielded 9,10-dihydro-4,5 -dimethoxy-9,10-dioxoanthracene-2-carbonyl azide as a signal yellow powder. Decomposition point: 139° C.

2) 9,10-Dihyro-4,5-dimethoxy-9,10-dioxoanthracene-2-isocyanate 9,10-Dihydro-4,5-dimethoxy-9,10-dioxoanthracene-2-carbonyl azide (3 g) was suspended in dry distilled 1,4-dioxan (200 ml) and heated to reflux under an atmosphere of nitrogen for 3 hours. The acyl azide completely dissolved during this time. Removal of solvent under reduced pressure yielded 9,10-dihydro-4,5-dimethoxy-9,10 -dioxoanthracene-2-isocyanate as an orange powder.

3) 2-Amino-9,10-dihydro-4,5-dimethoxy-9,10-dioxoanthrcene 9,10-Dihydro-4,5-dimethoxy-9,10-dioxoanthracene-2-isocyanate (5.50 g) was suspended in a solution of sodium hydroxide (3 g, excess) in water (100 ml) and heated to reflux for 30 minutes. During this time the orange suspension turned red. The mixture was cooled, the solid filtered off and washed with water (1×50 ml). Drying in vacuo over silica gel yielded 2-amino-9,10-dihydro-4,5-dimethoxy-9,10 -dioxoanthracene as a scarlet powder.

EXAMPLE 29

N-(9,10-Dihydro-4,5-dimethoxy-9,10-dioxoanthracen-2-yl)methanesuphonamide

2-Amino-9,10-dihydro-4,5-dimethoxy-9,10-dioxoanthracene (1.5 g) was dissolved in dry pyridine (30 ml) and freshly distilled methanesulphonyl chloride (0.61 g) slowly added. The mixture was heated to 90° C. for 3 hours under an atmosphere of nitrogen before being allowed to cool to room temperature. The mixture was then poured into water (150 ml), generating a brown precipitate. The solid was collected by filtration and dried in vacuo over silica gel to yield N-(4,5-dimethoxy-9,10-dihydro-9,10-dioxoanthracen-2 -yl)methanesulphonamide at 94% purity (HPLC) as brown lustrous crystals. To improve purity, the crystals were dissolved in 2N sodium hydroxide solution, washed with $CHCl_3$, and filtered to remove any remaining solid residue.

The aqueous filtrate was acidified with 2N hydrochloric acid, generating a precipitate. This solid was collected by filtration and dried in vacuo over silica gel to yield the sulphonamide as a mustard-coloured powder in 98+% purity (HPLC), decomposition point 233° C.

EXAMPLE 30

2-Amino-9,10-dihydro-4,5-dihydroxy-9,10-dioxoanthracene

2-Amino-9,10-dihydro-4,5-dimethoxy-9,10-dioxoanthracene (1 g) was suspended in a 48% solution of hydrobromic acid in water (30 ml) and heated to reflux under an atmosphere of nitrogen for sixty hours. The red suspension turned brown. The mixture was poured into water (100 ml), creating a red precipitate which was collected by filtration. Drying in vacuo over silica gel yielded 2-amino-9,10-dihydro-4,5-dihydroxy-9,10-dioxoanthracene as a dark red powder, m.p. 250°–252° C.

EXAMPLE 31

N-(9,10-Dihydro-4,5-dihydroxy-9,10-dioxoanthracen-2-yl)methanesulphonamide

N-(9,10-Dihydro-4,5-dimethoxy-9,10-dioxoanthracen-2-yl)methanesulphonamide (1.45 g) was suspended in a 48% solution of hydrobromic acid in water (30 ml) and heated to reflux under an atmosphere of nitrogen for 60 hours. The mixture was poured into water (100 ml) generating a precipitate which was collected by filtration. Drying in vacuo over silica gel yielded N-(9,10-dihydro-4,5-dihydroxy-9,10-dioxoanthracen-2-yl)methanesulphonamide at 92% purity (HPLC) as a brown powder, m.p. >300° C.

EXAMPLE 32

9,10-Dihydro-4,5-dimethoxy-9,10-dioxo-8-nitro-anthracene-2-carboxylic acid

Concentrated sulphuric acid (20 ml) was cooled to 5° C., and 9,10-dihydro-4,5 -dimethoxy-9,10-dioxoanthracene-2-carboxylic acid (1 g) was added portionwise during fifteen minutes, resulting in a deep crimson coloration. Maintaining the cool temperature, potassium nitrate (0.36 g) was added portionwise during 10 minutes. Stirring continued at 5° C. for a further 15 minutes before the mixture was allowed to warm to room temperature. Upon reaching room temperature, the mixture was heated to 40° C. for 1 hour. The material was then poured onto ice/water (100 ml), generating a yellow precipitate. This solid was collected by filtration and washed with water (1×100 ml). Drying in vacuo over silica gel yielded 9,10-dihydro-4,5 -dimethoxy-9,10-dioxo-8-nitro-anthracene-2-carboxylic acid as a signal yellow powder, decomposition point 230° C.

EXAMPLE 33

9,10-Dihydro-N-(4,5-diethoxy-9,10-dioxonthracen-2-yl)sulphamic acid

Sulphur trioxide pyridine complex (0.25 g) was suspended in dry pyridine (5 ml) and added to 2-amino-4,5-dimethoxy-9,10-dihydro-9,10-dioxoanthracene (0.44 g) dissolved in dry pyridine (10 ml). The mixture was heated to 90° C. for 1 hour under an atmosphere of nitrogen before being allowed to cool to room temperature. The mixture was poured into dilute hydrochloric acid (100 ml) and extracted into ethyl acetate (3×50 ml). The combined organic extracts were dried (MgSO₄) and solvents removed in vacuo to yield 9,10-dihydro-N-4,5-dimethoxy-9,10-dioxoanthracen-2-yl) sulphamic acid as a scarlet powder in 98.5% purity (HPLC), decomposition point 210° C.

EXAMPLE 34

9,10-Dihydro-4,5-dimethoxy-9,10-dioxo-N-hydroxy-N-methyl,anthracene-2-carboxamide A mixture of 9,10-dihydro-4,5-dimethoxy-9,10-dioxoanthracene-2-carboxylic acid (4.0 g), benzyltriethylammonium chloride (0.4 g) and thionyl chloride (4.6 ml) in 1,2-dichloroethane (150 ml) was stirred at reflux with the exclusion of moisture for 4 hours. The resulting brown solution was cooled and concentrated in vacuo to yield a green solid. This was evaporated with toluene (3×100 ml) and the solid suspended in dry dimethylformamide (100 ml). To this mixture cooled to 0° C. was added a slurry of N-methylhydroxylamine hydrochloride (2.0 g) in triethylamine (2 ml) and dimethyl formamide (20 ml). The mixture was stirred at 0° C. for 30 minutes and then allowed to warm to room temperature. After 16 hours at room temperature, the mixture was filtered and the filtrate diluted with water (400 ml). This was extracted with ethyl acetate (2×200 ml), the combined extracts washed with 2M hydrochloric acid (2×150 ml) and water (3×150 ml), dried (MgSO₄), filtered and evaporated to yield the impure product as a yellow-orange solid. This was triturated with dichloromethane, the insoluble material being filtered off, and the filtrate concentrated to yield the title compound as a yellow solid, m.p. 182° C.

EXAMPLE 35

N-Benzyloxy-4,5-diacetoxy-9,10-dihydro-9,10-dioxoanthracene-2-carboxamide

To a stirred solution of 4,5-diacetoxy-9,10-dihydro-9,10-dioxoanthracene-2 -carboxylic acid (6.14 g) in dry dimethylformamide (1.1 l) and nitrogen at −15° C. was added dropwise N-methylmorpholine (3.71 g) as a solution in dimethylformamide (20 ml) during 5 minutes. Stirring at −15° C. was continued for 40 minutes before the dropwise addition of isobutylchloroformate (2.51 g) as a solution in dimethylformamide (10 ml) over 10 minutes. The mixture was stirred at −15° C. for 45 minutes when a solution of O-benzylhydroxylamine hydrochloride (2.93 g) in dimethylformamide (20 ml) was added dropwise. Stirring was continued for 5 hours at −15° C. and the mixture was then allowed to warm to room temperature. After 16 hours at room temperature, the dark solution was concentrated in vacuo. The gummy residue was triturated with ethyl acetate to yield a bright yellow solid. This was triturated with tetrahydrofuran and the insoluble material then washed with 5% aqueous sodium bicarbonate solution. The insoluble yellow solid was washed with water and dried in vacuo yielding the title compound, m.p. 192°–194° C.

EXAMPLE 36

N-Benzyloxy-9,10-dihydro-4,5-dimethoxy-9,10-dioxo-N-methyl-anthracene-2-carboxamide To a stirred solution of 9,10-dihydro-4,5-dimethoxy-9,10-dioxoanthracene-2-carboxylic acid (2.00 g) in tetrahydrofuran (900 ml) at room temperature under nitrogen was added N-methyl morpholine (1.36 g) dropwise. The solution was then cooled to −15° C. and a solution of isobutylchloroformate (0.92 g) in tetrahydrofuran (5 ml) added during 5 minutes. The clear solution became cloudy. The mixture was stirred at −15° C. for 1 hour. To this was added portionwise over 5 minutes N-methyl O-benzylhydroxylamine hydrobromide (1.50 g). The cloudy mixture was stirred at −15° C. for 3 hours and then allowed to warm to room temperature. After 16 hours at room temperature, the mixture was filtered and the filtrate concentrated in vacuo. The resulting yellow solid was taken up in ethyl acetate (800 ml) and filtered to remove insolubles. The solution was washed with 10% aqueous sodium carbonate solution (three times), water (twice), dried (MgSO₄), filtered and evaporated to yield the title compound as a bright yellow powder, m.p. 170°–171° C.

EXAMPLE 37

1) 2-(2,5-Dimethoxy-4-methylbenzoyl)-3,6-dimethoxybenzoic acid 1,4-Dimethoxy-2-methylbenzene (4 g) was dissolved in dry dichloromethane (130 ml). To this stirred solution at ambient temperature was added aluminium chloride (7.1 g) followed by 3,6-dimethoxyphthalic anhydride (5.5 g), the stirring was maintained for 24 hours.

2M Hydrochloric acid was added to the chilled solution. Two clear phases were obtained. These were separated, and the organic phase was washed with concentrated hydrochloric acid, washed with brine, and then extracted into a solution of potassium carbonate (8 g) in water (130 ml). The aqueous extract was washed with a little chloroform, filtered, acidified with concentrated hydrochloric acid to give a cream solid which was filtered, washed with water, and dried. This solid contained the required acid as a mixture of rotamers. Melting points could vary from approximately 125° C. to 151° C. for different batches depending on the composition of this mixture.

Similarly prepared were:
2-(2,5-Dimethoxy-4-methylbenzoyl)benzoic acid, which was usually associated with its isomer 2-(2,5-dimethoxy-3-methylbenzoyl)benzoic acid, m.p. 136°–141° C., depending on the composition of the mixture.

2) 3,6-Dimethoxybenzene-1,2-dicarboxylic acid

To a solution of 3,6-dimethoxybenzene-1,2-dinitrile (20 g) in ethanol (200 ml) and water (100 ml) was added an aqueous solution of sodium hydroxide (100 ml, 10M) and the suspension heated at reflux for 24 hours, allowed to cool and the ethanol removed under reduced pressure. Water (120 ml) was added and the mixture stirred in an ice/water bath while concentrated hydrochloric acid was added in 1 ml portions until pH1 reached. The product was collected by filtration, washed with water and dried at 50° C. in a vacuum oven to given a white solid, m.p. 185°–186° C.

3) 3,6-Dimethoxyphthalic anhydride 3,6-Dimethoxybenzene-1,2-dicarboxylic acid (20 g) was dissolved in pyridine (100 ml) at room temperature. The solution was then cooled in a cold water bath and acetic anhydride (27 g, 25 ml) added dropwise over 10 minutes (temperature rose from 23° to 25° C.) The reaction mixture was then stirred for 90 minutes at 12° C., filtered, washed with ether (100 ml) and pulled dry to give a pale cream solid. Dried at 50° C. in a vacuum oven, m.p. 268°–269° C.

4) 2-(2,5-Dimethoxy-4-methylbenzoyl)-3,6-dimethoxybenzoic acid

To a stirred slurry of anhydrous aluminium chloride (35.9 g) in 1,2-dichloroethane (430 ml) at room temperature was added 3,6-dimethoxyphthalic anhydride (16 g) and the slowly forming bright orange mixture was stirred under nitrogen for 2 hours. A solution of 1,4-dimethoxy-2-methylbenzene (23.4 g) in 1,2-dichloroethane (80 ml) was added and the solution stirred under nitrogen for 4 hours. A further portion of 1,4-dimethoxy-2-methylbenzene (11.7 g) in 1,2-dichloroethane (50 ml) was then added and the mixture stirred at room temperature for 48 hours.

The dark orange brown solution was poured onto ice (2000 ml)/dilute hydrochloric acid (500 ml, 2M) to give a pale yellow mixture, which was diluted with dichloromethane (2000 ml), separated, and the aqueous phase washed twice with dichloromethane (2×500 ml). The bulked organic phase was then washed with saturated brine solution (1000 ml), extracted with aqueous potassium carbonate (3×1300 ml each containing 8 g potassium carbonate). The bulked basic phase was washed with dichloromethane (500 ml), then acidified with concentrated hydrochloric acid to pH1, filtered, washed with water (250 ml) and pulled dry to give a pale cream solid. Dried at 50° C. in a vacuum oven, m.p. 220°–222° C.

5) 9,10-Dihydro-9,10-dioxo-2-methyl-1,4,5,8-tetramethoxyanthracene
[known literature compound J. Org. Chem. 1979, 44 (26), 4802–4808]

A rotameric mixture of 2-(2,5-dimethoxy-4-methylbenzoyl)-3,6-dimethoxybenzoic acid (7 g) was stirred in concentrated sulphuric acid (50 ml) at ambient temperature for 24 hours. The dark green solution was quenched in ice and water and extracted into chloroform. This organic extract was washed with sodium bicarbonate solution, dried with magnesium sulphate, filtered and evaporated. The orange residue was dissolved in 2-butanone (150 ml) and heated under reflux in the presence of dimethyl sulphate (6.4 ml) and potassium carbonate (9.4 g) for 2 hours. The solution was filtered, evaporated to dryness, triturated with water, dried, dissolved in chloroform, filtered through a pad of silica-gel and evaporated. The residue was recrystallised from toluene to give yellow-orange crystals, m.p. 241.5°–242.5° C.

Similarly prepared was:
9,10-Dihydro-1,4-dimethoxy-9,10-dioxo-2-methylanthracene, m.p. 132° C. [known literature compound C.A. Vol. 9, Reg No. (52541-72-7)]

6) 9,10-Dihydro-9,10-dioxo-1,4,5,8-tetramethoxyanthracene-2-carboxylic acid

To a solution of potassium permanganate (6.7 g) in water (100 ml) was added a hot suspension of 9,10-dihydro-1,4,5,8-tetramethoxy-9,10-dioxo-2-methylanthracene (2.9 g) in tertiary butanol (100 ml). This mixture was heated under reflux for 24 hours. The solution was filtered and the filter pad washed with water, potassium carbonate solution, water and methanol. The combined filtrate was evaporated to near dryness, dissolved in water, filtered, washed with chloroform and acidified with concentrated hydrochloric acid. The solid was filtered off, washed with water and dried. This material was recrystallised from ethanol to give orange crystals, m.p. 236°–238° C.

Similarly prepared were:
9,10-Dihydro-9,10-dioxo-1,4,5-trimethoxyanthracene-2-carboxylic acid, m.p. 220°–223° C. from 1,4,5-trimethoxy-2-methyl anthrol [Tet Letts 1979, 4, 331–334].
9,10-Dihydro-1,4-dimethoxy-9,10-dioxoanthracene-2-carboxylic acid, m.p. 192°–194° C. from 9,10-dihydro-1,4-dimethoxy-9,10-dioxo-2-methyl-9,10-anthracene.

7) 9,10-Dihydro-9,10-dioxo-1,4,5-trihydroxyanthracene-2-carboxylic acid 9,10-Dihydro-9,10-dioxo-1,4,5-trimethoxy-anthracene-2-carboxylic acid (1.05 g) was dissolved in 45% hydrogen bromide-acetic acid mixture and heated for 2 hours. This solution was quenched in ice-water, a little ethanol was added to encourage coagulation of the colloidal suspension. The dark solid was filtered off and washed with water. This solid was suspended in water to which 2M sodium hydroxide was added and filtered off from insoluble material. The inky blue filtrate was acidified with concentrated hydrochloric acid. Ethanol was added again to coagulate the solid, which was filtered off, washed with water and triturated with ethanol to give an intense dark purple solid, m.p. >260° C.

Similarly prepared were:
9,10-Dihydro-1,4-dihydroxy-9,10-dioxoanthracene-2-carboxylic acid, m.p. 251°–253° C.

9,10-Dihydro-9,10-dioxo-1,4,5,8-tetrahydroxyanthracene-2-carboxylic acid m.p. >260° C.

8) 9,10-Dihydro-9,10-dioxo-1,4,5-trihydroxy-anthracene2-carboxylic acid 9,10-Dihydro-9,10-dioxo-1,4,5-triacetoxyanthracene-2-carboxylic acid (2.3 g) was heated under reflux in acetic anhydride (100 ml), with stirring, to which a 1:1 solution of concentrated sulphuric acid and acetic acid (four drops) was added. The reflux temperature was maintained for 30 minutes, during which time the solid dissolved to give a yellow solution. The solution was chilled, poured onto ice and water and the solution was agitated until a mustard yellow solid crystallised out. This was filtered off, washed thoroughly with water and then methanol, and dried, m.p. 179°–180° C.

Similarly prepared were:
9,10-Dihydro-9,10-dioxo-1,4,5,8-tetraacetoxyanthracene-2-carboxylic acid, m.p. 209°–211° C.
1-Acetoxy-9,10-dihydro-9,10-dioxo-4-hydroxyanthracene-2-carboxylic acid, m.p. 163°–165° C.
1,4-Diacetoxy-9,10-dihydro-9,10-dioxoanthracene-2-carboxylic acid, m.p. 174°–176° C.

EXAMPLE 38

1) 4-(5-Fluoro-2-methoxy phenyl)butanoic acid

4-Fluoroanisole (20 g) and ethyl succinyl chloride (28 g) were dissolved in nitromethane (70 ml). The solution was cooled in an ice +water bath and stirred under nitrogen. Aluminium chloride was added (30 g in 3×10 g portions) over 30 minutes. The cooling bath was removed and the reaction mixture was stirred under nitrogen for 5 hours. The reaction mixture was poured onto ice and extracted into ethyl acetate. The organic phase was collected and concentrated under reduced pressure. The crude product was taken up in ethyl acetate (150 ml) and washed with 2N sodium hydroxide solution (2×100 ml). The organic phase was dried over magnesium sulphate, filtered and the solvent removed under reduced pressure. The product was dissolved in acetic acid (200 ml) containing 47% perchloric acid (10 ml) and hydrogenated over 10% palladium on charcoal until two equivalents of hydrogen were taken up. The reaction mixture was filtered and concentrated under reduced pressure. The crude product was taken up in ethyl acetate and water. Sodium hydrogen carbonate was added until no reaction occurred then the organic phase was collected, dried and filtered. The solvent was removed at reduced pressure and the resulting dark oil was dissolved in methanol (120 ml). Sodium hydroxide (8 g) was added and the mixture was heated under reflux for 3 hours. Water (50 ml) was added and the mixture was washed with 1:1 ether/hexane (150 ml). The aqueous phase was acidified and the product was extracted into ethyl acetate. The organic phase was dried, filtered and evaporated under reduced pressure to give the product (19.5 g), as a dark oil that solidified on standing.

2) 8-Fluoro-5-methoxy-1-tetralone 4-(5-Fluoro-2-methoxy phenyl)butanoic acid (15 g) was mixed with polyphosphoric acid (60 g) and stirred with an overhead stirrer. The reaction mixture was heated to 90° C. and stirred at this temperature for 45 minutes. The reaction mixture was allowed to cool, water (100 ml) and ethyl acetate (100 ml) were added. The mixture was neutralised with sodium hydrogen carbonate solution, the organic phase was collected. The aqueous phase was extracted with ethyl acetate (2×100 ml). The combined organic extracts were dried over magnesium sulphate, filtered and concentrated under reduced pressure to give the crude product. This material was recrystallised from hexane-15% ethyl acetate to give the clean product.

3) 8Fluoro-1-hydroxy-5-methoxy-naphthalene

8-Fluoro-5-methoxy-l-tetralone (20 g) was dissolved in isopropenyl acetate (70 ml), p-toluenesulphonic acid (1 g) was added and the mixture was heated under reflux under nitrogen for 5 days. The reaction mixture was poured into aqueous sodium hydrogen carbonate solution (250 ml) and the crude product extracted into ethyl acetate (3×100 ml). The combined organic extracts were dried over magnesium sulphate, filtered and the solvent removed under reduced pressure. The resulting dark oil was taken up into dioxan (200 ml) and dichlorodicyanobenzoquinone (DDQ) (25 g) was added. The solution was heated under reflux for 18 hours and filtered to remove DDQ residues. The solvent was removed under reduced pressure and the crude product purified by chromatography on silica (eluent hexane/ethyl acetate 3:1). The resulting red oil was dissolved in methanol (100 ml) and heated under reflux with sodium hydroxide (9 g) for 1 hour. Water (100 ml) was added and the mixture was washed with ether/hexane 1:1 (200 ml). The aqueous phase was acidified and the product collected by filtration to give a dark solid after drying.

4) 8-Fluoro-5-methoxy-1,4-naphthaquinone

1-Hydroxy-5-methoxy-8-fluoronaphthalene (2.3 g) was dissolved in acetonitrile/water (9:1) (60 ml). The solution was stirred at room temperature and bis (trifluoroacetoxy) iodobenzene (6.45 g) was added portionwise. The reaction mixture was stirred for 16 hours and then the solvent was removed under reduced pressure. The crude product was purified by flash silica chromatography (eluent hexane/ EtOAc 3:2) to give the pure product as an orange/yellow solid, m.p. 136°–138° C.

5) 8-Fluoro-5-hydroxy-1,4-naphthaquinone

8-Fluoro-5-methoxy-1,4-naphthaquinone (300 mg) was added to a solution of aluminium chloride (1.5 g) in nitromethane at 0° C. The solution was stirred under nitrogen for 3 hours and then poured into cold dilute hydrochloric acid (100 ml). The solution was extracted with ethyl acetate (3×50 ml) and the combined organic extracts were dried (magnesium sulphate), filtered and concentrated under reduced pressure to give the product as a dark solid.

6) E-Ethyl 3-carboxaldehydobut-2-enoate ethylene acetal

E-Ethyl 3-carboxaldehydobut-2-enoate (20 g), dry ethylene glycol (17.5 g) and p-toluenesulphonic acid (trace) were dissolved in toluene (100 ml) and heated to reflux under Dean-Stark conditions for 3 hours. The mixture was then cooled and washed with saturated sodium 10 bicarbonate solution (1×50 ml). The toluene phase was dried (MgSO$_4$) and solvent removed in vacuo to yield E-ethyl 3-carboxaldehydobut-2-enoate ethylene acetal as a yellow oil.

7) 1-Ethoxy-1-tert-butyldimethylsilyloxy)-buta-1,4-diene-3-carboxaldehyde ethylene acetal Lithium di-i-propylamide mono(tetrahydrofuran) (32 ml, 1.5M in cyclohexane, 48 mmol) was diluted with dry THF (20 ml) and cooled to −78° C. N,N'-Dimethylpropyleneurea (12.4 g) was then added and the mixture was stirred for 5 minutes. After this time, E-ethyl 3 -carboxaldehydobut-2-enoate ethylene acetal (6.0 g), dissolved in dry THF (25 ml), was admitted dropwise, and stirring continued at −78° C. for 30 minutes, resulting in a deep red solution. tert-Butyldimethylsilyl chloride (4.9 g), dissolved in dry THF (20 ml), was then admitted dropwise and stirring was continued for a further 15 minutes at −78° C. before the mixture was allowed to warm to room temperature during several hours. The mixture was diluted with n-hexane (100 ml) and washed with saturated sodium bicarbonate solution (1×50 ml). The aqueous washings were back-extracted with n-hexane (1× 50 ml). The combined organic extracts were washed with water (4× 50 ml) and with brine (1×50 ml), before being dried ($K_2CO_3$). Solvents were removed in vacuo to yield 1-ethoxy-1-(tert-butyldimethylsilyloxy)-buta- 1,4-diene-3-carboxaldehyde ethylene acetal as an orange oil in 80–90% purity by $^1H$ n.m.r. Attempts to purify this material further by distillation or column chromatography all led to degradation.

8) 9,10-Dihydro-4,5dihydroxy-9,10-dioxo-8-fluoroanthracene-2-carboxylic acid

8-Fluoro-5-hydroxy-1,4-naphthaquinone (2 g) and 1-ethoxy-1-(tert-butyldimethylsilyloxy)-buta- 1,4-diene-3-carboxaldehyde ethylene acetal (3.6 g) were mixed under nitrogen in toluene (50 ml) and heated under reflux for 15 hours. The solvent was removed under reduced pressure to leave a dark oil. This material was dissolved in acetonitrile containing 40% aqueous hydrogen fluoride (9:1) (50 ml) and stirred for 4 hours at room temperature. The solvent was removed under reduced pressure and replaced with 30% aqueous acetic acid (60 ml). The reaction mixture was heated under reflux for 20 hours. The solvent was removed under reduced pressure and the dark oily product was dissolved in dimethyl sulphoxide (30 ml). Sodium dihydrogen phosphate (500 mg) in water (3 ml) was added. Sodium chlorite (2.5 g) dissolved in water (10 ml) was added dropwise over one hour. The reaction mixture was stirred for 15 hours and poured into water. A precipitate separated and was collected by filtration. The collected solid was dissolved in hot methanol and purified by preparative scale HPLC (eluent 30% water in methanol, 0.1% acetic acid, LP1-ODS, Hichrom) to give the pure product.

$^1H$ n.m.r. ($d^6DMSO$) 7.48 1H (dd), 7.75 (1H) dd, 7.77 1H (d), 8.10 1H (d). High resolution MS—calculated for $C_{15}H_8FO_6$ 303.03049, found 303.03283 deviation 7.7 ppm.

EXAMPLE 39

8-Fluoro-2-formyl-5-methoxytetralone

Sodium hydride (12.7 g) (50% dispersion, washed with hexane) was suspended in dry THF under nitrogen. Ethyl formate (27 g) was added and the mixture was stirred for 20 minutes in an ice/water bath. 5-Methoxy-8-fluoro-1-tetralone (J. Med. Chem. (1973) 1003) (17 g) dissolved in THF was added and the mixture was allowed to warm to room temperature. The mixture was stirred under nitrogen for 24 hours. Methanol was added followed by water. The mixture was poured into water, acidified with conc. HCl (aq) and extracted into $CHCl_3$. The organic phase was dried ($MgSO_4$), filtered and concentrated to give a dark oil (22 g) which solidified on standing. This material was recrystallised from ethyl acetate/hexane to give the above compound, m.p. 66°–68° C.

8-Fluoro-1-hydroxy-5-methoxynaphthlene-2-carboxaldehyde

8-Fluoro-2-formyl-5-methoxy-1-tetralone (20 g) was dissolved in dioxan. 2,3-Dichloro-5,6-dicyanobenzoquinone (21 g) was added and the mixture was heated under reflux for 2 hours. The mixture was allowed to cool and was filtered to remove solids. The solvent was removed under reduced pressure and the residue taken up in ethyl acetate. The product solution was washed with saturated $NaHCO_3$ (aq) (×3), dried ($MgSO_4$), filtered and evaporated to give a dark solid. This material was recrystallised from ethyl acetate/hexane to give 1-hydroxy-5-methoxy-8-fluoro-2-naphthaldehyde, m.p. 156°–158° C.

1,5-Dimethoxy-8-fluoronaphthalene-2-carboxaldehyde

8-Fluoro-1-hydroxy-5-methoxy-2-naphthalene-2-carboxaldehyde (5.6 g) was dissolved in dry MeCN under nitrogen. Potassium carbonate (5 g) and iodomethane (7.5 g) were added and the mixture was heated under reflux with vigorous stirring for 2 hours. The solution was filtered to remove solids and concentrated down. The residue was taken up in ethyl acetate and washed with water (×2). The organic phase was dried ($MgSO_4$), filtered and evaporated to a yellow solid (5.75 g). This material was recrystallised from ethyl acetate/hexane to give 1,5-dimethoxy-8-fluoro-2-naphthaldehyde, m.p. 129°–131° C.

tert-Butyl 3-carboxyethyl-3-phosphonodiethyl propionate

Triethylphosphonacetate (dried over anhydrous $MgSO_4$) (49.28 g) in dry THF (150 ml) was added dropwise with stirring under nitrogen at 0° C. during 30 minutes to hexane (200 ml) washed 50% sodium hydride (11.074 g, 5.537 g) in dry THF (300 ml) and the mixture stirred overnight. After this time 'butylbromoacetate (45 g) was added dropwise at 0° C. under nitrogen during 30 minutes then allowed to warm at room temperature overnight. The solvent was reduced in vacuo to approximately 60 ml (viscous white solution of NaBr in organic solvent) then poured into water/ethyl acetate (200+500 ml). The aqueous was separated and extracted with ethyl acetate (2×250 ml), combined with ethyl acetate (to give 800 ml of EtOAc), washed with brine (200 ml), dried ($MgSO_4$), filtered and evaporated in vacuo to give a pale yellow liquid which was distilled in two fractions (120°–132° C. then 132° C.) which both resulted in the required product in a high purity.

3-Carboxyethyl-4-(1,5-dimethoxynaphthalen-2-yl)-but-3-enoic acid

Tert-butyl 3-carboxyethyl-3-phosphono diethyl propionate (7.5 g) was dissolved in dry THF under nitrogen and cooled in an ice/water bath. Lithium diisopropylamide solution (15 ml, 1.5N) was added and the solution was allowed to stir for 20 minutes. 1,5-Dimethoxy-8-fluoro-2-naphthaldehyde (5 g) in dry THF was added and the mixture was allowed to warm to room temperature. The reaction mixture was stirred for 24 hours and water was added. The solution was concentrated under reduced pressure and partitioned between water and dichloromethane. The organic phase was collected, dried ($MgSO_4$), filtered and evaporated under reduced pressure to a dark oil (10.9 g). This product was taken up in trifluoroacetic acid/water 9:1 (30 ml) and stirred for 2 hours at room temperature. The solvent was removed under reduced pressure and carbon tetrachloride was added. This was removed under reduced pressure and the residue was dissolved in sat. $Na_2CO_3$ (aq) solution. The aqueous solution was washed with diethyl ether, acidified (2N HCl (aq)) and extracted with dichloromethane. The organic phase was dried ($MgSO_4$), filtered and concentrated to give 4(2'-(1,5 -dimethoxy-8-fluoro-naphthyl)-3-carboxyethyl-but-3-enoic acid.

Ethyl 4-acetoxy-5,10-dimethoxy-8-fluoroanthracene-2-carboxylate

4(2'-(1,5-Dimethoxy-8-fluoro-naphthyl))-3-carboxyethyl-but-3-enoic acid (7 g) was dissolved in acetic anhydride (30 ml) with anhydrous sodium acetate (6 g). The reaction mixture was heated under reflux with vigorous stirring under nitrogen for 18 hours. The reaction mixture was allowed to cool and was poured onto ice. The mixture was neutralised ($Na_2CO_3$) and extracted with ethyl acetate (4×100 ml). The organic phase was dried ($MgSO_4$), filtered and concentrated to a dark oil. Column chromatography on silica gel (eluent ethyl acetate/hexane) gave a yellow solid, 1-acetoxy-3 -carboxyethyl-5,9-dimethoxy-6-fluoro anthracene.

Ethyl 4-hydroxv-6,10-dimethoxy-9-fluoroanthracene-2-carboxylate

4-Acetoxy-2-carboxyethyl-6,10-dimethoxy-9-fluoroanthracene (5 g) was dissolved in ethanol at room temperature and a solution of sodium ethoxide in ethanol was added. The reaction mixture was stirred for 30 minutes, then acidified with 2N HCl (aq). The solvent was removed under reduced pressure, the residue was taken up in the ethyl acetate and washed with water. The solution was dried (MgSO$_4$) and filtered, hexane was added and a yellow solid precipitated on cooling, ethyl 4-hydroxy-6,10-dimethoxy-9-fluoroanthracene-2-carboxylate).

Ethyl 9-fluoro-4,6,10-trimethoxyanthracene-2-carboxylate

Ethyl 4-hydroxy-6,10-dimethoxy-9-fluoroanthracene-2-carboxylate (4 g) was dissolved in acetonitrile. Potassium carbonate (2.5 g) and iodomethane (3 g) were added. The mixture was heated under reflux with vigorous stirring under nitrogen for 2 hours. The solution was filtered to remove solids and washed with water. The organic phase was washed, dried (MgSO$_4$), filtered and concentrated to give the above compound as a yellow solid.

Ethyl 9,10-dihydro-4,5-dimethoxy-9,10-dioxo-8-fluoroanthracene-2-carboxylate 4,6,10-Trimethoxy-2-carboxyethyl-9-fluoroanthracene (3 g) was dissolved in acetone (20 ml) and cooled in an ice-water bath. Sodium dichromate (3 g) was dissolved in 30% aq. sulphuric acid (10 ml) and was added dropwise to the stirred acetone solution. The reaction mixture was allowed to warm to room temperature. After 2 hours 2-propanol (5 ml) was added and the mixture was poured into ethyl acetate. The resulting solution was washed with brine, dried (MgSO$_4$), filtered and concentrated under reduced pressure to a red oily solid (3.5 g). This solid was dissolved in acetonitrile and heated under reflux with potassium carbonate (2 g) and dimethyl sulphate (1.5 g). This After 2 hours the mixture was filtered and concentrated to a red oil. was purified by column chromatography on silica gel (eluent-ethyl acetate/hexane) to give a yellow solid, m.p. 201°–203° C.

EXAMPLE 40

Methyl 3,6-difluoro-9,10-dihydro-4,5-dimethoxy-9,10-dioxoanthracene-2-carboxylate and methyl 9,10-dihydro-4,5-dimethoxy-9,10-dioxo-6-fluoroanthracene-2-carboxylate A suspension of methyl 9,10-dihydro-4,5-dimethoxy-9,10-dioxoanthracene-2carboxylate (10 g) and 'Selectfluor' (21 g) in dry acetonitrile (125 ml) was stirred at an oil bath temperature of 85° C. for 10 days. Additional portions of 'Selectfluor' were added during this time (8 g after 66 hours, 6.9 g after 90 hours, 6.1 g after 140 hours). The suspension was allowed to cool and the solid filtered off and washed well with dichloromethane. The red filtrate was concentrated to yield a solid (18 g). This was suspended in dichloromethane (50 ml) and passed through a 4"×3" pad of flash silica, eluting with ethyl acetate. This yielded a yellow foam that was rechromatographed on silica with ethyl acetate/hexane (1:1) eluant yielding firstly methyl 3,6-difluoro-9,10-dihydro-4,5-dimethoxy-9,10-dioxoanthracene 2-carboxylate, m.p. 204.5°–206° C. and methyl 9,10-dihydro-4,5-dimethoxy-9,10-dioxo-6-fluoroanthracene-2-carboxylate, m.p. 199°–201° C., both as fluffy yellow solids.

EXAMPLE 41

9,10-Dihydro-4,5-dihydroxy-9,10-dioxo-6-fluoro-anthracene 2-carboxylic acid

A suspension of methyl 4,5-dimethoxy-6-fluoro-9,10-dihydro-9,10-dioxoanthracene 2-carboxylate (306 mg) in 47% aqueous hydrobromic acid was stirred at reflux for 18 hours. The yellow suspension was cooled and concentrated to yield a yellow solid. This was triturated with water, filtered, washed well with water and dried to yield 9,10-dihydro-4,5-dihydroxy-9,10-dioxo-6-fluoro-anthracene 2-carboxylic acid as a deep yellow solid, m.p. >275° C.

EXAMPLE 42

9,10-Dihydro-4,5-dimethoxy-9,10-dioxoanthracene-2-[N-2-(nitrophenyl)]carboxamide 9,10-Dihydro-4,5-dimethoxy-9,10-dioxoanthracene-2-carboxylic acid (4 g) was suspended in 1,2-dichloroethane (30 ml). Benzyltriethylammonium chloride (0.4 g) was added, followed by thionyl chloride (7.56 g). The mixture was magnetically stirred and heated under reflux for 5 hours 20 minutes, during which time complete dissolution occurred.

The solvent and excess thionyl chloride were removed by evaporation in vacuo to leave a light brown solid, which was subsequently suspended in dry toluene (28 ml) together with 2-nitroaniline (1.42 g). The mixture was stirred and heated under reflux for 1 hour 5 minutes.

The suspension was evaporated in vacuo to leave a dark brown gum, which was then stirred briefly in a boiling mixture of acetone (150 ml) and water (50 ml). After standing at room temperature for 1.5 hours, the resulting mustard coloured solid was removed by filtration and dried at 120° C. in vacuo.

Recrystallisation of this solid from nitrobenzene (40 ml) at 110° C. yielded 2.63 g of the pure carboxamide, m.p. 237°–238° C., after washing with 40°–60° C. petroleum ether and drying at 100° C. in vacuo.

EXAMPLE 43

4,5-Diacetoxy-9,10-dihydro-9,10-dioxoanthracene-2-[N-4-(methyl phenyl)]carboxamide 4,5-Diacetoxy-9,10-dihydro-9,10-dioxoanthracene-2-carboxylic acid (6 g) was suspended in thionyl chloride (58.14 g). Anhydrous pyridine (2.5 ml) was added and the mixture was magnetically stirred under reflux for 2.8 hours. The resulting solution was evaporated at 45° C. in vacuo to leave a yellow/brown solid. Dry toluene (50 ml) was added, then evaporated at 50° C. in vacuo to remove any remaining thionyl chloride. To the residue was added a solution of p-toluidine (1.75 g) in dry toluene (75 ml) and the mixture was stirred and heated under reflux for 35 minutes.

After cooling to room temperature the mixture was filtered to remove a mustard coloured solid, which was washed with cold toluene (50 ml) then 40°–60° C. petroleum ether (50 ml) before drying at 110° C. in vacuo.

The dried solid (6.19 g) was solute extracted with toluene (250 ml) for 26 hours. After cooling to room temperature the extract was diluted with 40°–60° C. petroleum ether (200 ml) and kept in an ice-bath for 0.5 hours. The resulting mustard coloured solid was removed by filtration and washed with 40°–60° C. petroleum ether (50 ml) before drying at 110° C. in vacuo.

The solid (4.1 g) was dissolved in boiling dioxan (150 ml). Water (50 ml) was added to produce turbidity and stirring was continued for 0.75 hours at ambient temperature. After standing overnight the mustard coloured solid was removed by filtration, then stirred in 50% aqueous ethanol (60 ml) for a few minutes. The suspension was filtered and the solid washed with water (50 ml) before drying at 110° C. in vacuo to give the pure carboxamide, m.p. 271°–273° C.

EXAMPLE 44

9,10-Dihydro-4,5-dihydroxy-9,10-dioxoanthracene-2-[N-2-(trifluoromethyl)phenyl]carboxamide A suspension of 4,5-diacetoxy-9,10-dihydro-9,10-dioxoanthracene-2-carboxylic acid (6 g) in thionyl chloride (35.7 ml, 58.14 g) and anhydrous pyridine (2.5 ml) was stirred and heated under reflux for 3.5 hours.

After evaporation at 56° C. in vacuo to leave a yellowy brown solid, a solution of 2-aminobenzotrifluoride (2.63 g) in dry toluene (75 ml) was added. The mixture was heated and stirred under reflux for 1 hour, then allowed to stand at room temperature overnight.

The suspension was filtered to remove a dark brown solid, which was washed on the filter with 40°–60° C. petroleum ether (2×50 ml) before drying at 110° C. in vacuo.

The solid was solute extracted with toluene (approximately 200 ml) for 48 hours, and the extract was allowed to cool to room temperature.

A pale green coloured solid, 3 g, was obtained after filtration, washing with 40°–60° C. petroleum ether (2×50 ml) and drying at 110° C. in vacuo.

The solid was dissolved with stirring, in boiling dioxan (100 ml), then filtered hot through a 1 cm pad of decolourising charcoal. The filter contents were washed with hot dioxan (20 ml). The filtrate and washings were combined, diluted with water (50 ml) and kept in an ice-bath for 15 minutes before removing a yellow solid by filtration.

The filtrate was evaporated in vacuo to leave the yellow carboxamide, which was then dried at 110° C. in vacuo, m.p. >310° C.

EXAMPLE 45

N-Acetyl-4,5-diacetoxy-9,10-dihydro-9,10-dioxoanthracene-2-[N-2 -(trifluoromethyl)phenyl]carboxamide A suspension of 9,10-dihydro-4,5-dihydroxy-9,10-dioxoanthracene-2-[N-2 -(trifluoromethyl)phenyl]carboxamide (0.89 g) in acetic anhydride (4.5 ml) and anhydrous pyridine (2 ml) was magnetically stirred and heated in an oil-bath at bath temperature 100° C.±1° for 2.5 hours.

The solution was poured onto crushed ice (40 ml), when a gum precipitated. On scratching the gum solidified. The resulting cream coloured solid was removed by filtration and washed with water (150 ml) before drying at 65° C. in vacuo.

The solid was again treated with acetic anhydride (4 ml) and anhydrous pyridine (2 ml) for 19 hours at bath temperature of 86° C.

After allowing to cool the solution was poured into water (75 ml). The resulting triacetylated carboxamide was removed by filtration, washed with water (200 ml) and dried at 75° C. in vacuo, m.p. 210°–212° C.

EXAMPLE 46

Di-O-isopropyl-2-(9,10-dihydro-4,5-dimethoxy-9,10-dioxoanthracen-2 -yl)ethenyl phosphonate Tetraisopropyl methylene diphosphonate (1.931 g) was dissolved in dry tetrahydrofuran (50 ml). n-Butyl lithium (3 ml) was added dropwise and the mixture allowed to stir under nitrogen for 15 minutes. At 0° C. 9,10-dihydro-4,5-dimethoxy-9,10-dioxoanthracene-2-carboxyaldehyde (1.204 g) was added as a tetrahydrofuran (100 ml) solution over 5 minutes. The mixture was warmed to room temperature then refluxed for 16 hours.

The mixture was cooled and water (40 ml) was added before the mixture was concentrated in vacuo. The aqueous residues were extracted with dichloromethane (4×100 ml) separated and dried over magnesium sulphate. Inorganics were filtered off and the organic solution was concentrated in vacuo to yield a dark oil. The oil was triturated with ether (10 ml) and the resulting mustard coloured solid was filtered and washed with ether (2×10 ml). Then dried under vacuum at 65° C., m.p. 132°–134° C.

EXAMPLE 47

Di-O-isopropyl-2-(9,10-dihydro-4,5-dihydroxy-9,10-dioxoanthracen-2 -yl)ethenyl phosphonate Tetraisopropyl methylene diphosphonate (0.839 g) was dissolved in tetrahydrofuran (20 ml) and magnetically stirred under nitrogen. n-Butyl lithium (1.1 ml) was added dropwise to this mixture at room temperature. This mixture was continually stirred before being added dropwise to the following mixture at 0° C.

9,10-Dihydro-4,5-dimethoxy-9,10-dioxoanthracene-2-carboxyaldehyde (0.503 g) was added to a suspension of 50% sodium hydride (0.190 g) in tetrahydrofuran (80 ml) and dimethylsulphoxide (8 ml). The resulting purple solution was allowed to stir for 2 hours before the 'diphosphonate' anion (described above) was added dropwise at 0° C. The combined mixtures were warmed to room temperature and then heated to reflux. The mixture was stirred at reflux for 16 hours.

After cooling to room temperature, the mixture was poured onto 2N hydrochloric acid (150 ml). The resulting orange precipitate was filtered and dried under vacuum at 65° C., m.p. 168°–170° C.

EXAMPLE 48

2-(9,10-Dihydro-4,5-dihydroxy-9,10-dioxoanthracen-2-yl)ethenyl phosphonic acid

Di-O-isopropyl-2-(9,10-dihydro-4,5-dihydroxy-9,10-dioxoanthracen-2 -yl)ethenyl phosphonate (1.00 g) was suspended in 47% aqueous hydrobromic acid, was heated at reflux for 1.5 hours. The solution was cooled, poured onto water (150 ml), filtered and dried at 50° C. to give a pale mustard solid, m.p. >260° C.

EXAMPLE 49

Hydrogen isopropyl-2-(9,10-dibydro-4,5-dihydroxy-9,10-dioxoanthracen-2 -yl)ethenyl phosphonate A stirred mixture of di-O-isopropyl-2-(9,10-dihydro-4,5-dihydroxy-9,10 -dioxoanthracen-2-yl)ethenyl phosphonate (1.0 g) dioxane (20 ml) and 2M sodium hydroxide solution (50 ml) was heated at reflux for 2 hours. The resulting solution was allowed to cool to room temperature and then cooled in an ice/water bath and acidified to pH 2 by dropwise addition of 10N hydrochloric acid. The mixture was diluted with brine (50 ml) and extracted with dichloromethane (5×50 ml). The organic layers were combined, washed with brine (2×50 ml) then dried over MgSO$_4$ and concentrated in vacuo. The resulting oil/foam was stirred at 100° C. in toluene (40 ml), decanted from a tarry residue, then cooled to 5° C. The solid was collected by filtration, washed with toluene (20 ml) then ether (20 ml) and dried in vacuo at 25° C., m.p. 183°–186° C. (dec.)

EXAMPLE 50

2-(9,10-Dihydro-4,5-dimethoxy-9,10-dioxoanthracen-2-yl)ethenyl phosphonic acid

Di-O-methyl-2-(9,10-dihydro-4,5-dimethoxy-9,10-dioxoanthracen-2-yl)ethenyl phosphonate (0.900 g) was dissolved in dry dichloromethane (20 ml). This solution was magnetically stirred under nitrogen. At 0° C. bromotrimethylsilane (0.6 ml) was added dropwise. This mixture was warmed to room temperature and stirred for 2 hours before methanol (10 ml) was added. The resulting yellow precipitate was stirred overnight before being filtered and washed with methanol (5 ml). The solid was dried under vacuum at

EXAMPLE 51

1) 5-(Triphenylmhosphoniomethyl)tetrazolide

A stirred suspension of cyanomethyltriphenylphosphonium chloride (13.5 g), sodium azide (5.2 g) and ammonium chloride (4.28 g) in dimethylformamide (40 ml) was heated and stirred at 120° C. for 1.5 hours, cooled, poured into saturated sodium hydrogen carbonate solution (100 ml) and ice (100 g). The solution was basified to pH10 and the resultant white precipitate was isolated by filtration to give a white solid (8.3 g). This solid was dissolved in hot ethanol (50 ml) and filtered. On cooling, ethyl acetate (100 ml) then diethyl ether (100 ml) were added and the resultant white precipitate isolated by filtration to give 5.3 g of the betaine, m.p. 280° C.

2) 5-(2-(9,10-Dihydro-4,5-dimethoxy-9,10-dioxonathracen-2-yl)ethen-1-yl)-tetrazole Potassium carbonate (0.376 g) was added to a suspension of 9,10-dihydro-4,5-dimethoxy-9,10-dioxoanthracene-2-carboxaldehyde (0.538 g) and 5-(triphenylphosphoniomethyl)tetrazolide (0.75 g) in methanol (20 ml) and heated and stirred under reflux under nitrogen for 24 hours, and then allowed to cool. The solvent was evaporated in vacuo and the residue acidified with hydrochloric acid (2M, 50 ml), and the precipitated solid isolated by filtration and air dried. This solid was washed on the sinter with dichloromethane (5×80 ml) and air dried to give the above compound as a fawn solid, m.p. 228°–230° C.

The following formulations of active compounds of the invention can be prepared.

EXAMPLE 52

Soft gelatin capsule
Each soft gelatin capsule contains:

| | |
|---|---|
| Active ingredient | 150 mg |
| Arachis oil | 150 mg |

After mixing together, the blend is filled into soft gelatin capsules using the appropriate equipment.

EXAMPLE 53

Hard gelatin capsule
Each capsule contains:

| | |
|---|---|
| Active ingredient | 50 mg |
| PEG 4000 | 250 mg |

The PEG 4000 is melted and mixed with the active ingredient. Whilst still molten the mixture is filled into capsule shells and allowed to cool.

EXAMPLE 54

Tablets each containing 10 mg of active ingredient are made up as follows:

| | |
|---|---|
| Active ingredient | 10 mg |
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

We claim:

1. A compound of the formula

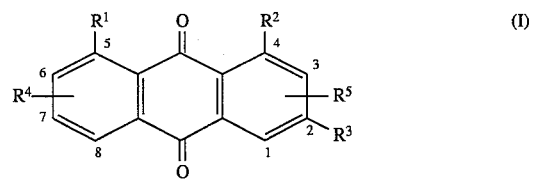

in which $R^3$ is tetrazolyl, $R^1$ and $R^2$ are each hydroxyl, halo, $C_{1-4}$ alkoxy, acyloxy, —O-glucoside, optionally substituted phenyl or optionally substituted phenyl-$C_{1-4}$ alkoxy, and $R^4$ and $R^5$ are each hydrogen, hydroxy, acyloxy, nitro, $C_{1-4}$ alkyl, $C_{1-4}$ alkoxy, halo, optionally substituted phenyl, —$SO_3H$, or —NR'R" where R' and R" are each hydrogen or $C_{1-4}$ alkyl, or a salt or ester thereof.

2. A compound according to claim 1, in which $R^1$ and $R^2$ are each hydroxyl, halo, $C_{1-4}$ alkoxy, acyloxy, —O-glucoside or optionally substituted phenyl, and $R^4$ and $R^5$ are each hydrogen, hydroxy, nitro, $C_{1-4}$ alkyl, $C_{1-4}$ alkoxy, optionally substituted phenyl or —NR'R" where R' and R" are each hydrogen or $C_{1-4}$ alkyl.

3. A compound according to claim 1, in which $R^1$ and $R^2$ are each hydroxyl, $C_{1-4}$ alkoxy or acyloxy, and $R^4$ and $R^5$ are each hydrogen, hydroxy, acyloxy, $C_{1-4}$ alkoxy or halo.

4. A compound according to claim 3, in which $R^4$ and $R^5$ are hydrogen.

5. A compound according to claim 4, which is 5-(4,5-diacetoxy-9,10-dihydro-9,10-dioxoanthracen-2-yl)tetrazole.

6. A method for treating osteoarthritis and allied connective tissue matrix diseases in a patient, which comprises administering to said patient an effective amount of a compound of claim 1.

7. The method of claim 6, for treating osteoarthritis.

8. The method of claim 6, for treating rheumatoid arthritis.

9. A pharmaceutical composition comprising a pharmaceutically acceptable diluent or carrier in association with a compound of claim 1, or a pharmaceutically acceptable salt or ester thereof.

* * * * *